US008071535B2

(12) United States Patent
Tor et al.

(10) Patent No.: US 8,071,535 B2
(45) Date of Patent: Dec. 6, 2011

(54) GUANIDINIUM DERIVATIVES FOR IMPROVED CELLULAR TRANSPORT

(75) Inventors: Yitzhak Tor, San Diego, CA (US); Nathan Luedtke, Branford, CT (US)

(73) Assignee: The Regents of the University of California, Oakland, CA (US)

( * ) Notice: Subject to any disclaimer, the term of this patent is extended or adjusted under 35 U.S.C. 154(b) by 975 days.

(21) Appl. No.: 10/571,510

(22) PCT Filed: Sep. 10, 2004

(86) PCT No.: PCT/US2004/029880
§ 371 (c)(1),
(2), (4) Date: Dec. 8, 2006

(87) PCT Pub. No.: WO2005/025513
PCT Pub. Date: Mar. 24, 2005

(65) Prior Publication Data
US 2007/0185040 A1    Aug. 9, 2007

Related U.S. Application Data

(60) Provisional application No. 60/502,385, filed on Sep. 12, 2003.

(51) Int. Cl.
*A61K 31/70* (2006.01)
*A61K 38/00* (2006.01)
*C07H 15/22* (2006.01)
*C08B 5/10* (2006.01)
*C08B 11/00* (2006.01)

(52) U.S. Cl. ............... 514/1.1; 514/37; 514/39; 514/41; 514/43; 536/13.2; 536/13.6; 536/13.7; 536/22.1

(58) Field of Classification Search ................ 536/13.2, 536/13.6, 13.7, 22.1
See application file for complete search history.

(56) References Cited

U.S. PATENT DOCUMENTS

| 4,160,452 | A | 7/1979 | Theeuwes |
| 4,256,108 | A | 3/1981 | Theeuwes |
| 4,265,874 | A | 5/1981 | Bonsen et al. |
| 4,749,800 | A | 6/1988 | Jobe et al. |
| 6,525,182 | B1 * | 2/2003 | Goodman et al. ........... 536/13.2 |

FOREIGN PATENT DOCUMENTS

WO    WO 2005/025513    3/2005

OTHER PUBLICATIONS

International Search Report and Written Opinion dated Jul. 20, 2005 for PCT/US04/29880, filed Sep. 10, 2004, (8 pages).

Baba, M. et al., "HIV-1-Specific Reverse Transcriptase Inhibitors," Chapter 11 in Anti-Aids Drug Development: Challenges, Strategies and Prospects, P. Mohan and M. Baba (Editors), Harwood Academic Publishers GmbH, Switzerland, 1995, pp. 239-267.
Baker, T.J. et al., "Synthesis and Anti-HIV activity of Guanidinoglycosides," J. Org. Chem., 65: 9054-9058 (2000).
Check, E., "HIV Drug Resistance Triggers Strategic Switch," Nature 424: 361 (Jul. 24, 2003).
De Clercq, Erik, "From Anti-HIV Agents to Anti-AIDS Chemotherapy: A Critiical Appraisal," Chapter 1 in Anti-AIDS Drug Development: Challenges, Strategies and Prospects, P. Mohan and M. Baba (Editors), Harwood Academic Publishers GmbH, Switzerland, 1995, pp. 1-37.
Frankel, A.D. and J.A.T. Young, "HIV-1: Fifteen Proteins and an RNA," Annu. Rev. Biochem. 67: 1-25 (1998).
Greenwald, R.B. et al., "Drug Delivery Systems employing 1,4- or 1,6-Eliminations: Poly(ethylene glycol) Prodrugs of Amino-containing Compounds," J. Med. Chem. 42: 3657-3667 (1999).
Jeong, L.S. et al., "Nucelosides and Derivative," Chapter 2 in Anti-AIDS Drug Development: Challenges, Strategies and Prospects, P. Mohan and M. Baba (Editors), Harwood Academic Publishers GmbH, Switzerland, 1995, pp. 39-63.
Kirk, S.R. et al., "Neomycin-Acridine Conjugate: A Potent Inhibitor of Rev-RRE Binding," J. Am. Chem. Soc. 122: 980-981 (2000).
Luedtke, N.W. and Y . Tor, "A Novel Solid-Phase Assembly for Identifying Potent and Selective RNA Ligands," Angew. Chem. Int. Ed. 39(10): 1788-1790 (2000).
Luedtke, N.W. et al., "Guanidinoglycosides: A Novel Family of RNA Ligands," J. Am. Chem. Soc. 122: 12035-12036 (2000).
Pollard, V.M. and M.H. Pollard, "The HIV-1 Rev Protein" Annu. Rev. Microbiol. 52: 491-532 (1998).
Joint United Nations Programme on HIV/AIDS (UNAIDS), *Report on the Global HIV/AIDS Epidemic 2002*, Switzerland, UNAIDS/02. 26E, ISBN 92-1973-185-4 , 229 pages (Jul. 2002).
Wakselman, M., "1,4- and 1,6-eliminations from hydroxyl and and amino-substituted benzyl systems: chemical and biochemical applications," Nouveau Journal De Chimie, 7(7): 439-447 (Jul. 1983).
Wang, H. and Y. Tor, "Dimeric Aminoglycosides: Design, Synthesis and RNA Binding," Bioorganic & Medicinal Chemistry Letters, 7(14): 1951-1956 (1997).
Wang, H. and Y. Tor, "Tobramycin-EDTA Conjugate: A Noninnocent Affinity-Cleaving Reagent,", Bioorg. Med. Chem. Lett. (1998) 8: 3665-3670 (1998).
Wang, H. and Y. Tor, "Electrostatic Interactions in RNA Aminoglycosides Binding," J. Am. Chem Soc. 119:8734-8735 (1997).

* cited by examiner

*Primary Examiner* — Elli Peselev
(74) *Attorney, Agent, or Firm* — Fish & Richardson P.C.

(57) ABSTRACT

Reagents and methods useful for the synthesis of conjugates comprising guanidinylated cyclic acetals are provided. Also provided are methods for increasing the cellular uptake of various therapeutic compounds and treatment modalities using these conjugates.

27 Claims, 8 Drawing Sheets

GUANIDINIUM DERIVATIVES FOR IMPROVED CELLULAR TRANSPORT

CROSS REFERENCE TO RELATED APPLICATIONS

This application is a 35 USC §371 National Stage application of PCT Application No. PCT/US2004/029880 filed Sep. 10, 2004; which claims the benefit under 35 USC §119(e) to U.S. Application Ser. No. 60/502,385 filed Sep. 12, 2003, now abandoned. The disclosure of each of the prior applications is considered part of and is incorporated by reference in the disclosure of this application.

BACKGROUND OF THE INVENTION

1. Field of the Invention

The invention relates generally to bioavailability and delivery of therapeutic molecules and, more specifically, to guanidinylated cyclic acetals and conjugation of such modified acetals to therapeutic compounds to increase the cellular uptake of the therapeutic compounds.

2. Background Information

Charged molecules over 500 attomicron typically exhibit poor bioavailability. This limits the delivery of many therapeutically active molecules to their intended targets. Polycationic molecules provide important exceptions to this generalization. Modification of Bovine Serum Albumin (BSA) with ethylene diamine produces "cationionized BSA", a highly effective antigen carrier. Despite its size (over 66,000 attomicron), cationized BSA efficiently enters cells via an unknown path involving adsorptive uptake. More recently, a number of poly-arginine peptides, peptoids, and peptidomimetics, have been found to exhibit highly efficient uptake into a wide range of mammalian cell types. The conjugation of such poly-Arg peptides to large molecules can facilitate the transduction of peptide, protein, and nucleic acid, conjugates into cells. The mechanism responsible for poly-Arg mediated transport is still unclear, but may involve a receptor mediated, non-endocytotic route.

Thus, an opportunity exists for exploiting such a poly-arginine peptide-like transduction mechanism for efficient uptake of therapeutically active molecules by eukaryotic cells.

SUMMARY OF THE INVENTION

The present invention is based on the discovery that guanidineglycoside containing conjugates can exhibit enhanced cellular uptake at target cells, and thus may be useful in the delivery of therapeutic compounds for treatment of variety of diseases and disorders.

In one embodiment, a method of increasing the cellular uptake of a compound is provided which includes conjugation of a compound with a molecule having a modified cyclic acetal. The acetal can be guanidinylated. In one aspect, such an acetal may be polymeric or non-polymeric. In a related aspect, a method of making such conjugates is also envisaged.

In another related aspect, the modified cyclic acetal is a natural or synthetic glycoside and, more particularly includes, but is not limited to, aminoglycosides, cardiac glycosides, disaccharides or other polysaccharides. Further, primary or secondary alcohol or primary or secondary amines of these glycosides can be reacted with guanidinylating reagents to produce guanidinoglycosides. In one embodiment, such guanidinoglycosides can be covalently bonded to molecules of interest, including therapeutically active molecules.

In a related aspect, guanidinylated cyclic acetal containing compounds include, but are not limited to, amikacin, gentamicin, kanamycin, neomycin, netilmicin, O-2,6-Diamino-2,6-dideoxy-beta-L-idopyranosyl-(1 to 3)-O-beta-D-ribofuranosyl-(1 to 5)-O-[2-amino-2-deoxy-alpha-D-glucopyranosyl-(1 to 4)]-2-deoxystreptamine, streptomycin, tobramycin, ouabain, deslanoside, digoxin, digitoxin, lantoside, gitoxigenin, bufalin and strophanthin.

Further, compounds covalently conjugated to the guanidinoglycosides of the present invention may include, but are not limited to, nucleic acids, nucleosides, proteins, peptides, amino acid residues, lipids, carbohydrates, synthetic organic compounds, metals, vitamins, small molecules, dyes, isotopes, antibodies, toxins ligands or any other compound that may need transport into a cell.

In one embodiment, the conjugates include, but are not limited to, a nucleoside, such as a reverse transcriptase inhibitor (RTI). In a related aspect, such nucleosides may include, but are not limited to, 3'-azido-3'-deoxythymidine, 2',3'-dideoxyinosine and 2',3'-dideoxycytidine. In another related aspect, the reverse transcriptase inhibitor is conjugated to a guanidine-modified aminoglycoside, such as guanidino-amikacin, guanidino-gentamicin, guanidino-kanamycin, guanidino-neomycin, guanidino-netilmicin, guanidino-O-2,6-Diamino-2,6-dideoxy-beta-L-idopyranosyl-(1 to 3)-O-beta-D-ribofuranosyl-(1 to 5)-O-[2-amino-2-deoxy-alpha-D-glucopyranosyl-(1 to 4)]-2-deoxystreptamine, guanidino-streptomycin and guanidino-tobramycin.

DETAILED DESCRIPTION OF THE INVENTION

Figure 1:
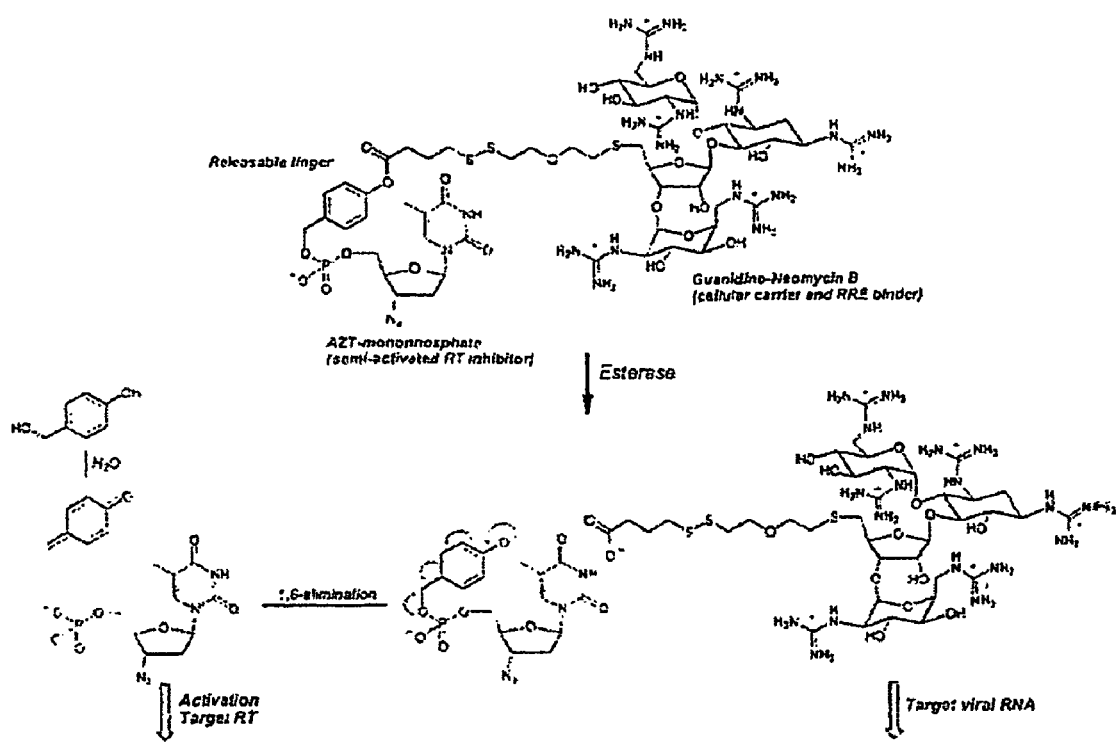
FIG. 1 illustrates a representative structure of a three component conjugate.

The present invention provides guanidinoglycoside-containing conjugates which exhibit enhanced cellular uptake at target cells. Such conjugates are useful in the delivery of therapeutic compounds for a number of diseases and disorders including, but not limited to, viral infections (e.g., retroviral infections associated with HIV, HBV, and the like), bacterial infections, and disorders associated with, for example, inappropriate mitogenic signaling, non-insulin-dependent diabetes, and inhibition of enzymes including thrombin, glycosidases, and nitric oxide synthases.

The term "alkyl" used herein refers to a monovalent straight or branched chain radical of from one to ten carbon atoms, including, but not limited to, methyl, ethyl, n-propyl, isopropyl, n-butyl, isobutyl, tert-butyl, n-hexyl, and the like.

Alkyl also represents cyclic radicals, including, but not limited to cyclopropyl, cyclobutyl, cyclopentyl, cyclohexyl, and the like.

The term "cationionized" used herein refers to the process of modifying a compound with a molecule such that the surface of the compound is positively charged.

The term "perfluoroalkyl" as used herein refers to a monovalent straight chain radical of from one to four carbon atoms, in which all hydrogen atoms are substituted by fluorine. A typical perfluorinated alkyl group is the trifluoromethyl group.

The term "aryl" when used alone refers to an aromatic radical whether or not fused. Preferred aryl groups include phenyl, naphthyl, biphenyl and the like. Aryl also refers to heteroaromatic groups including, but not limited to, furanyl, pyrrolyl, thienyl, pyrazolyl, thiazolyl, oxazolyl, pyridyl, pyrimidinyl, indolyl, and the like.

The term "substituted aryl" as used herein refers to an aryl group substituted with one, two or three substituents chosen from halogen, cyano, nitro, $C_1$-$C_{10}$ alkyl, $C_1$-$C_{10}$-alkoxy, trifluoromethyl, alkoxycarbonyl, and the like. Examples of such groups are 4-chlorophenyl, 2-methylphenyl, and 3-ethoxyphenyl.

The term "arylalkyl" as used herein refers to one, two or three aryl groups having the designated number of carbons, appended to an alkyl chain having the number of carbons designated. A typical arylalkyl group is the benzyl group.

The term "alkenyl" as used herein refers to a straight or branched chain group of from two to ten carbon atoms containing a carbon-carbon double bond, including, but not limited to allyl, vinyl, and the like.

The term "acetal" as used herein is defined an organic compound that is a product of a reaction between an alcohol and an aldehyde. The general structure of an acetal can be illustrated as shown by the structure (I) below.

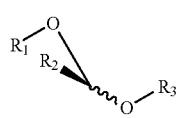
(I)

The term "cyclic acetal" as used herein is defined as an acetal in which at least one oxygen atom of an acetal is a part of a ring. In one embodiment, the structure of the cyclic acetal that can be used is encompassed by the structure (I) above, where the $R_1$, $R_2$, and/or $R_3$ groups comprise at least two 5- or 6-membered rings that are linked together by at least one acetal-type functional group where $R_1$-$R_2$, and $R_3$ are the carbon atoms of two separate ring systems.

The term "ketal" as used herein is defined an organic compound that is a product of a reaction between an alcohol and ketone. The general structure of a ketal can be illustrated as shown by the structure (II) below, in which each of R and $R_1$ is, independently, hydrogen or alkyl, and each of $R_2$ and $R_3$ is an alkyl.

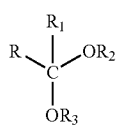
(II)

The term "dialkoxy compounds" as used herein is defined as compounds having two alkoxy groups attached to the same carbon. Accordingly, the term "dialkoxy compounds" is used herein as inclusive of both acetals illustrated by the formula (I) and ketals illustrated by formula (II) shown above.

The term "guanidine" as used herein is defined as a substance having the general structure (III):

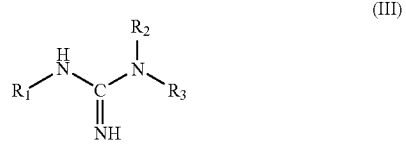
(III)

wherein each of $R_1$, $R_2$ and $R_3$ is, independently, hydrogen or a lower alkyl group, e.g., a $C_1$-$C_3$ alkyl.

Accordingly, wherever the term "guanidine" is used herein, the term is inclusive of unsubstituted guanidine (each of $R_1$, $R_2$ and $R_3$ in structure (III) is hydrogen) and of an alkylguanidine (at least one of $R_1$, $R_2$ and $R_3$ in structure (III) is a lower alkyl group).

The term "guanidine group" or "guanidine moiety" as used herein is defined as a group or moiety derived from either unsubstituted guanidine or from an alkylguanidine, as defined above.

The term "guanidinylated acetal" as used herein is defined as an acetal having a guanidine moiety attached to it. The embodiments of the present invention include guanidinylated cyclic acetal reagents as discussed below. These guanidinylated cyclic acetal reagents can be used in the synthesis of conjugates for the transport/uptake of compounds into eucaryotic cells. Guanidinylating reagents and general methods for producing guanidinoglycosides are defined and described in U.S. Pat. No. 6,525,182, the disclosure of which is herein incorporated by reference in its entirety.

The abbreviation "Boc" refers to tert-butyxocarbonyl group.

The term "BODIPY" is a trade name of one of a family of fluorescent dyes available from Molecular Probes, Inc. (Eugene, Oreg.).

The abbreviation "TIPS" refers to 2,4,6-triisopropylbenzenesulfonyl moiety.

The term "parenteral administration" as used herein includes administration by subcutaneous injections, aerosol, intravenous, intramuscular, intrathecal, intracranial, intrasternal injection or infusion techniques.

Embodiments of the present invention are directed to methods of achieving an increased cellular uptake of therapeutically beneficial compounds. The methods include modifying a dialkoxy compound with a substance having a guanidine group, such as guanidine or alkylguanidine, to form an adduct, followed by conjugating a therapeutically beneficial compound to the adduct to form a conjugate, and by delivering the conjugate to a cell. The dialkoxy compounds, which can be modified by guanidine, include acetals and ketals, for example, cyclic acetals.

Some embodiments of the present invention relate to compounds covalently conjugated to guanidinoglycosides that exhibit efficient uptake by eukaryotic cell cultures. The mechanism of the uptake may be similar to that exhibited by cationionized peptides. In a related aspect, such conjugated products may share the same uptake mechanism as the TAT and other arginine-containing peptides.

Other embodiments of the present invention relate to the conjugates themselves and methods of using such conjugates in treating patients. Such treatments may include, but are not limited to, modalities where delivery of nucleic acids, nucleosides, proteins, peptides, amino acid residues, lipids, carbohydrates, synthetic organic compounds, metals, vitamins, small molecules, dyes, isotopes, antibodies, toxins ligands or any other compound that may need transport into a cell is required. In one embodiment, conjugates may be administered to patients having bacterial or viral infections, including administering conjugates comprising guanidinoglycosides in amounts sufficient to inhibit or prevent such infections. In a related aspect, conjugates containing reverse transcriptase (RT) inhibitors (RTI) for the treatment of HIV are also envisaged.

In one embodiment, the efficacy of cellular uptake for molecules conjugated to the guanidinoglycosides of the present invention can be enhanced for anti-HIV of nucleoside based RTIs. In a related aspect, efficacy for such RTIs can be enhanced by covalently conjugating their monophosphates to guanidinoglycosides. In another embodiment, where RT inhibitors can be actively transported into the cell and then released in a semi-active (and potentially fully activated) form, the necessary monophosphorylation step can be circumvented. In one embodiment, essential regulatory events involving viral specific protein RNA interactions (e.g., Rev RRE) are inhibited. Thus, in a related aspect, two distinct stages in the life cycle of the virus are targeted with one anti-HIV agent. An example of this strategy is illustrated in FIG. 1 discussed below.

In one embodiment, the affinity of guanidinoglycosides to viral RNA sequences and their cellular uptake features have resulted in the formulation of a strategy where hybrid molecules containing a nucleotide analog conjugated to a guanidinoglycoside are proposed as "double warhead" anti-HIV agents.

In one related aspect, the invention can be used to enhance the therapeutic factor of clinically proven nucleoside reverse transcriptase inhibitors (NRTIs) by reducing the number of metabolic activation steps needed, including but not limited to, increasing negatively charged nucleotide residence in the cell. In another aspect, NRTIs that have failed to be metabolically activated may be given new clinical applications as novel formulations. Such new and effective anti-HIV agents may be produced at low cost and low market price.

Examples of cyclic acetals that can be used include the generic structures (IV) and (V) shown below.

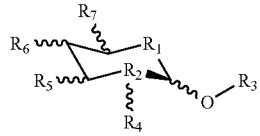

(IV)

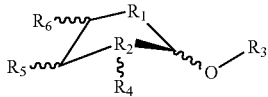

(V)

In the structures (IV) and (V), two or more rings are linked by at least one cyclic acetal, where $R_1$ and $R_2$ must be either carbon or oxygen atoms that compose a natural or synthetic glycoside (cyclic acetal), including, but not limited to, aminoglycosides, cardiac glycosides, dissacharides, or other polysacchrides.

In one embodiment, $R_3$ is a 5 or 6-membered ring (or series of rings linked by acetal linkages) that is either an additional glycosidic unit(s), or alternatively, a substituted hexane or pentane ring (where both the $R_1$ and $R_2$ groups are carbon atoms). One or more of the carbon atoms that compose these 5- or 6-membered rings are directly substituted with one or more basic groups, where $R_4$-$R_7$ is an amine, guanidine, methylene, or alternatively, an acetal linkage to another ring system(s) that contains one or more of these functional groups.

In one embodiment, such substituted aminoglycosides are conjugated to therapeutic compounds. A representative retrosynthetic scheme showing one synthetic route conjugation is illustrated below (Scheme I).

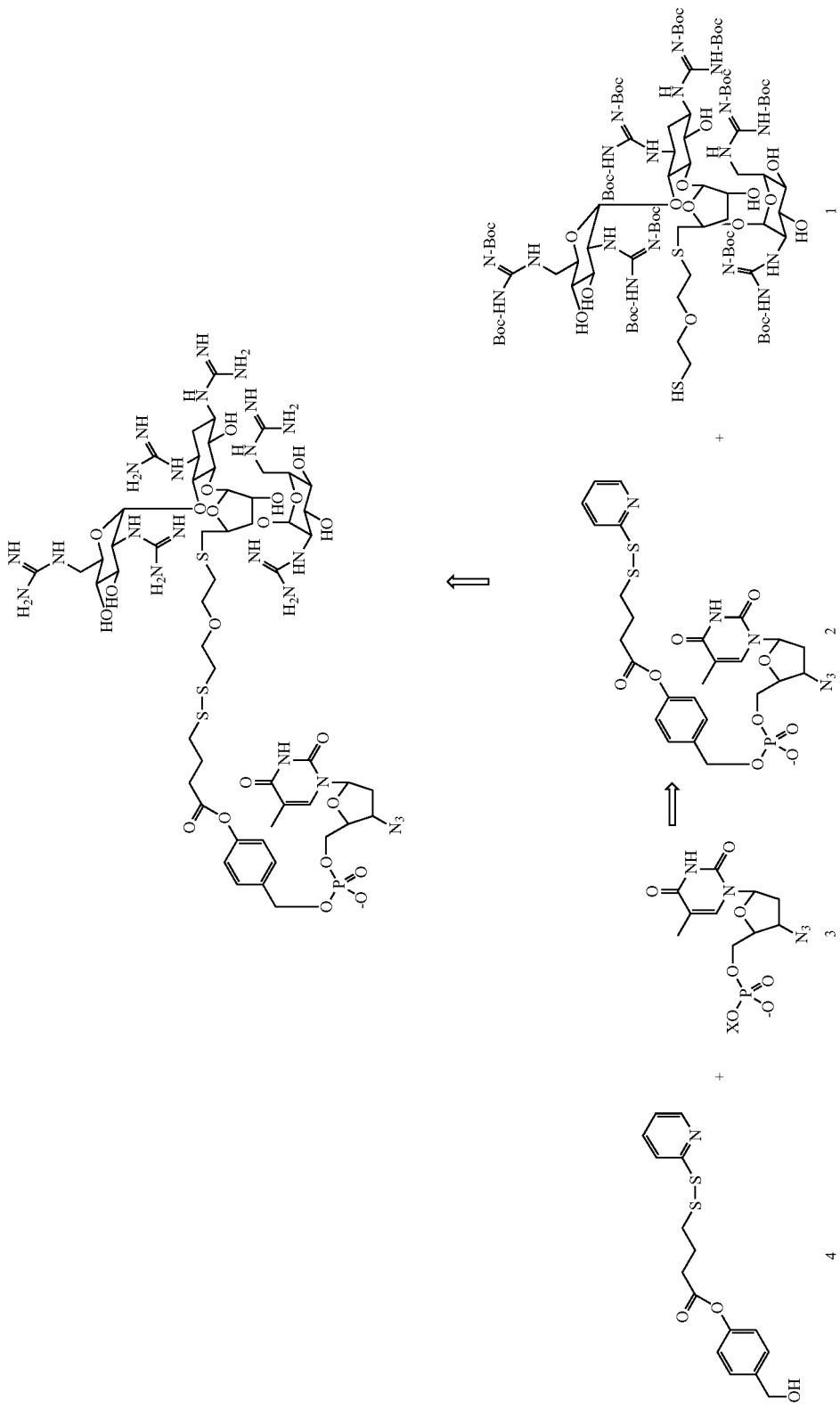

As shown by Scheme I, a fully-Boc protected guanidino-neomycin B (1) bearing a long thiol-containing linker can be conjugated via an effective thiol-exchange reaction with the extended AZT-linker conjugate (2). This "extended" AZT can be obtained by condensing the activated AZT-monophosphate (3) with the linker (4), which in turn can be obtained from commercially available building blocks via standard chemistry (e.g., SIGMA Chemical Co., St. Louis, Mo.). Synthesis of the various modified aminoglycosides, guanidinoglycosides and their conjugates is known in the art (see, e.g., U.S. Pat. No. 6,525,182; Wang et al., J. Am. Chem. Soc. (11997) 119:8734-8735; Wang et al., Bioorg. Med. Chem. Lett. (1997) 7:1951-1956; Kirk et al., J. Am. Chem. Soc. (2000) 122:980-981; Wang et al., Bioorg. Med. Chem. Lett. (1998) 8:3665-3670; Luedtke et al., J. Am. Chem. Soc. (2000) 122:12035-12036; and Baker et al., J. Org. Chem. (2000) 65:9054-9058). Several alternative building blocks are discussed below.

In one embodiment, the conjugate design facilitates a modular synthesis where the various components can be separately synthesized and then coupled together in advanced stages. In a related aspect, this allows mixing-and-matching of various carriers/RRE binders with a variety of linkers and NRTI monophosphates.

The modular design of the proposed conjugates translates into significant flexibility in the synthetic approach. Numerous reagents and reaction conditions are available for each coupling step. The formation of the phosphodiester linkage between AZT monophosphate (3) and the linker (4), for example, can be facilitated by, but is not limited to, carbonyldiimidazole or via DMAP-catalyzed carbodiimide condensation.

In one embodiment, a conjugate can include three key functional components as shown by FIG. 1. The three components shown by FIG. 1 are (1) guanidine-neomycin B (cellular carrier); (2) AZT monophosphate; and (3) a releasable linker.

For example, for nucleoside-based RT inhibitor, as HIV reverse transcriptase (RT) is a low-fidelity DNA polymerase, it can be inhibited by nucleoside analogs that mimic deoxyribonucleoside triphosphates (dNTP), its natural substrates. In a related aspect, well-established inhibitors, such as 3'-azido-2',3'-dideoxythymidine (AZT) in their semi-activated form are envisaged as conjugated compounds.

In a further related aspect, to effectively release the semi-activated NRTI from its carrier/RRE binder, a hydrolysable linker may be employed. For example, an esterase-induced hydrolysis followed by a facile 1,6-elimination reaction that releases the NRTI-monophosphate in its intact form can be used (see e.g., FIG. 1).

In one embodiment, an RRE binder/membrane translocation vehicle is contemplated. The Rev-Response-Element (RRE) serves as the Rev-binding site responsible for the active export of unspliced and singly spliced HIV genomic RNA from the nucleus. Small organic molecules that target such unique viral RNA sites can prevent the formation of a key regulatory RNA-protein complex and interfere with viral replication. In a related aspect, the use of guanidino-neomycin B and guanidino-tobramycin is contemplated. These two derivatives have substantial affinity to the RRE (see, e.g., U.S. Pat. No. 6,525,182) and very effective cellular uptake profiles (see below).

In a related aspect, any NRTI-monophosphate can potentially be employed. Similarly, various linkers with different degradation mechanisms will be readily appreciated by one of skill in the art. Additionally, numerous guanidinoglycosides can be utilized. For example, natural or synthetic guanidino-sugars, or guanidinylated aminoglycoside derivatives can also be used. In one embodiment, the guanidinylated forms of dimeric aminoglycosides or the guanidylated products of aminoglycoside decomposition fragments and/or simple oligomers of these units are envisaged. In addition, modification of other (common) forms of saccharides including di-, tri-, and tetra-saccharides may also be suitable scaffolds for the presentation of guanidine groups. In one embodiment, for guanidinoglycosides, such modified forms may include, but are not limited to, guanidino-amikacin, guanidino-gentamicin, guanidino-kanamycin, guanidino-neomycin, guanidino-netilmicin, guanidino-O-2,6-Diamino-2,6-dideoxy-beta-L-idopyranosyl-(1 to 3)-O-beta-D-ribofuranosyl-(1 to 5)-O-[2-amino-2-deoxy-alpha-D-glucopyranosyl-(1 to 4)]-2-deoxystreptamine, guanidino-streptomycin and guanidino-tobramycin.

In another embodiment, for cardiac glycosides, such modified forms may include but are not limited to, guanidino-ouabain, guanidino-deslanoside, guanidino-digoxin, guanidino-digitoxin, guanidino-lantoside, guanidino-gitoxigenin, guanidino-bufalin and guanidino-strophanthin.

For amines, a typical reaction scheme can be as follows (Scheme II):

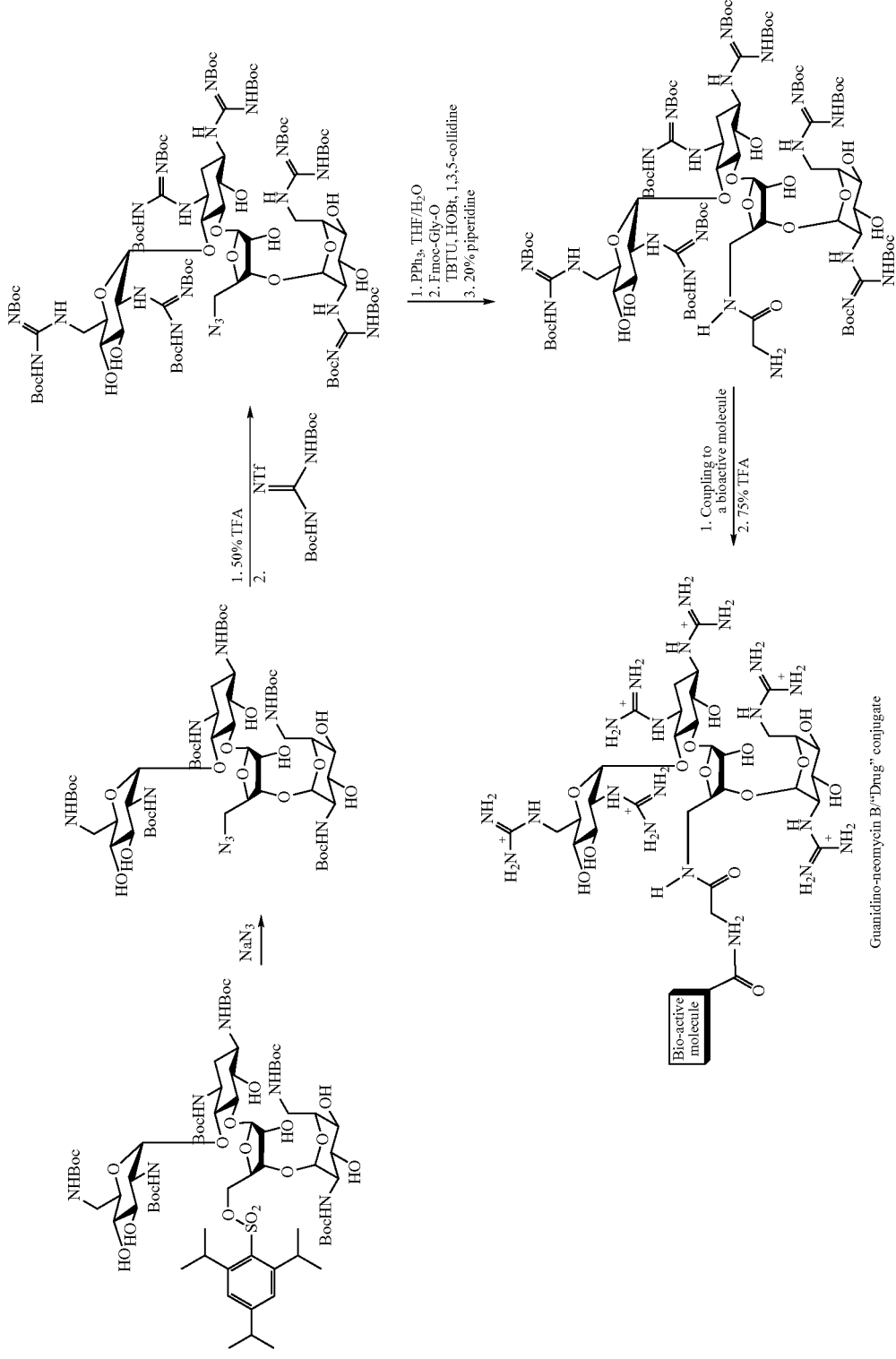

In one embodiment, the coupling of a bioactive molecule to a guanidinylated glycoside can be accomplished through an amino acid linker. In a related aspect, a 5"-TIPS activated Boc-protected neomycin B derivative can be reacted with sodium azide. The Boc groups can be then removed and the free amines can be reacted with a Boc-protected guanidinylating reagent (see, e.g., U.S. Pat. No. 6,525,182). Triphenol phosphine is then used to reduce the azido group into an amine. To this amine any bioactive molecule can be conjugated, with or without the use of a linker (e.g., nucleic acids, nucleosides, proteins, peptides, amino acid residues, lipids, carbohydrates, synthetic organic compounds, metals, vitamins, small molecules, dyes, isotopes, antibodies, toxins ligands or any other compound that may need transport into a cell). In one embodiment, the amino acid glycine can be used as a linker between the bioactive molecule and the guanidinylated glycoside. Those having ordinary skill in the art would recognize that other amino acids may be substituted.

For thiols, a typical reaction scheme can be as follows (Scheme III):

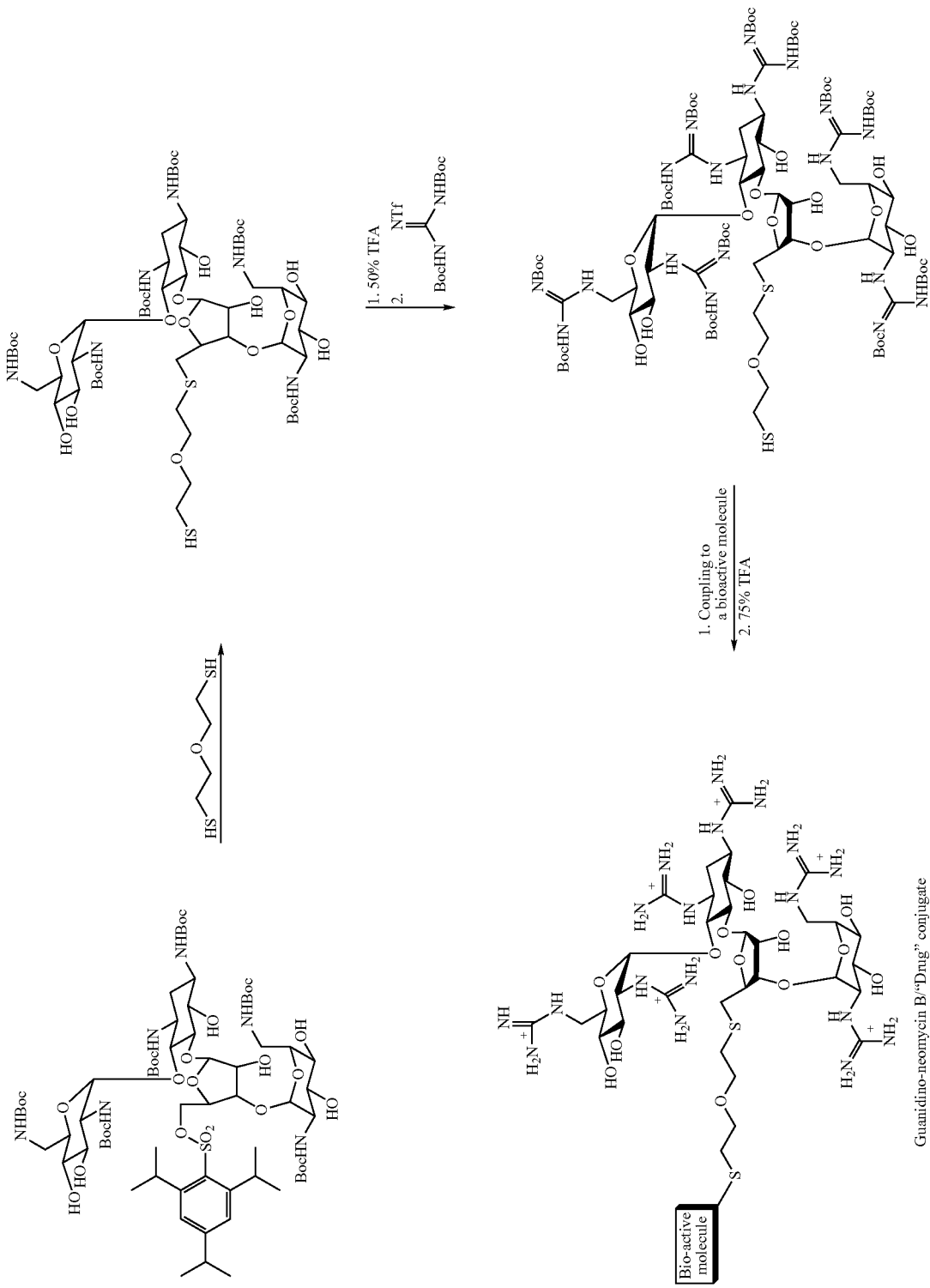

In one embodiment, the coupling of a bioactive compound to a guanidinylated glycoside can be accomplished through a thiol linker. In one aspect, a 5"-TIPS activated, Boc-protected neomycin derivative can be reacted with a dithiol. In one embodiment, the dithiol can be B-mercaptoethylether, but those having ordinary skill in the art would recognize that other similar dithiols may be used instead. The Boc groups can be then removed and the free amines are reacted with a Boc-protected guanidinylating reagent (see, e.g., U.S. Pat. No. 6,525,182). The coupling of the bioactive molecule through the free thiol can be performed either before or after the removal of the protecting groups (in the scheme above, Boc) from the guanidine groups. This allows for the coupling reaction to be conducted under aqueous or non-aqueous conditions (e.g., depending on the solubility and reactivity of the bioactive molecule).

In one embodiment, a reversed phase HPLC can be used for purifying the final product (for example, the presence of the useful thymidine chromophore for UV-detection can be utilized). In a related aspect, to facilitate the purification of intermediates, the guanidinoglycoside core can be maintained in its Boc-protected form. Such building blocks can be purified by normal phase chromatography.

As mentioned above, each functional component can be replaced by an alternative building block. In a related aspect, the parameters to be considered for advanced stages include the ability to tune the cellular uptake by using different guanidinoglycosides, the ability to tune the linker cleavage rate by substituting the benzene core in 4,9 or use other linkers with different release mechanisms, and the ability incorporate alternative nucleoside analogs.

In one embodiment, a method for treating a subject having a bacterial or viral infection or treating a subject susceptible to infection with a bacteria or virus is provided. The method includes administering a guanidinoglycoside-conjugate of the invention, an analogue, derivative, or salt thereof, prior to, simultaneously with, or subsequent to infection by a bacteria or viral organism.

In another embodiment, the invention provides a method of inhibiting or modulating the progression of viral infections (e.g., retroviral infections associated with HIV, HBV, and the like), bacterial infections, and disorders associated with, for example, inappropriate mitogenic signaling, non-insulin-dependent diabetes, and inhibition of disorders associated with thrombin, glycosidases, and nitric oxide synthases.

Thus, the guanidinoglycosides-containing conjugates of the present invention, as well as analogues, derivatives, or salts thereof are useful in the treatment of various maladies in general, either separately or in combination with other therapeutically active compounds. These compounds may be administered orally, topically or parenterally in dosage unit formulations containing conventional non-toxic pharmaceutically acceptable carriers, adjuvants, and vehicles.

The present invention also provides suitable topical, oral, and parenteral pharmaceutical formulations for use in the treatment of various illnesses. The compounds of the present invention may be administered orally as tablets, aqueous or oily suspensions, lozenges, troches, powders, granules, emulsions, capsules, syrups or elixirs. The composition for oral use may contain one or more agents selected from the group of sweetening agents, flavouring agents, colouring agents and preserving agents in order to produce pharmaceutically elegant and palatable preparations. The tablets contain the active ingredient in admixture with non-toxic pharmaceutically acceptable excipients which are suitable for the manufacture of tablets. These excipients may be, for example, (1) inert diluents, such as calcium carbonate, lactose, calcium phosphate or sodium phosphate; (2) granulating and disintegrating agents, such as corn starch or alginic acid; (3) binding agents, such as starch, gelatin or acacia; and (4) lubricating agents, such as magnesium stearate, stearic acid or talc. These tablets may be uncoated or coated by known techniques to delay disintegration and absorption in the gastrointestinal tract and thereby provide a sustained action over a longer period. For example, a time delay material such as glyceryl monostearate or glyceryl distearate may be employed. Coating may also be performed using techniques described in the U.S. Pat. Nos. 4,256,108; 4,160,452; and 4,265,874 to form osmotic therapeutic tablets for control release.

The guanidinoglycoside-conjugates of the invention (including analogues, derivatives, or salts thereof) can be administered, for in vivo application, parenterally by injection or by gradual perfusion over time independently or together. Administration may be intravenously, intraperitoneally, intramuscularly, subcutaneously, intracavity, or transdermally. For in vitro studies the agents may be added or dissolved in an appropriate biologically acceptable buffer and added to a cell or tissue.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, growth factors and inert gases and the like.

The labels in the present invention can be primary labels (where the label comprises an element which is detected directly) or secondary labels (where the detected label binds to a primary label, e.g., as is common in immunological labeling). Primary and secondary labels can include undetected elements as well as detected elements. Useful primary and secondary labels in the present invention can include spectral labels such as fluorescent dyes (e.g., fluorescein and derivatives such as fluorescein isothiocyanate (FITC) and Oregon Green™, rhodamine and derivatives (e.g., Texas red, tetrarhodintine isothiocynate (TRITC), and the like), dixogenin, biotin, phycoerytlrin, AMCA, CyDyes™, and the like), radiolabels (e.g., $^3$H, $^{125}$I, $^{35}$S, $^{14}$C, $^{32}$P, $^{33}$P, and the like), enzymes (e.g., horse-radish peroxidase, alkaline phosphatase, and the like) spectral calorimetric labels such as colloidal gold or colored glass or plastic (e.g., polystyrene, polypropylene, latex, and the like) beads. The label may be coupled directly or indirectly to Rev according to methods well known in the art. As indicated above, a wide variety of labels may be used, with the choice of label depending on sensitivity required, ease of conjugation with the compound, stability requirements, available instrumentation, and disposal provisions. In general, a detector is adapted to the particular label which is used. Typical detectors include X-ray machines, CAT scanners, NMR, spectrophotometers, phototubes and photodiodes, microscopes, scintillation counters, cameras, film and the like, as well as combinations thereof. Examples of suitable detectors are widely available from a variety of commercial sources known to persons of skill.

The examples of the labels that can be used include those which utilize (1) chemiluminescence (using horseradish peroxidase and/or alkaline phosphatase with substrates that produce photons as breakdown products) with kits being available, e.g., from Molecular Probes, Amersham, Boehringer-Mannhiem and Life Technologies/Gibco BRL; (2) color production (using both horseradish peroxidase and/or alkaline phosphatase with substrates that produce a colored precipitate; kits available from Life Technologies/Gibco BRL, and Boehringer-Mannheim); (3) hemifluorescence using, e.g., alkaline phosphatase and the substrate AttoPhos (Amersham) or other substrates that produce fluorescent products, (4) fluorescence (e.g., using Cy-5 (Amersham), fluorescein, and other fluorescent tags); and (5) radioactivity. Other methods for labeling and detection will be readily apparent to one skilled in the art.

The fluorescent labels that can be used are typically characterized by one or more of the following: high sensitivity, high stability, low background, low environmental sensitivity and high specificity in labeling. Fluorescent moieties, which can be incorporated into the labels of the invention include BODIPY, Texas red, dixogenin, biotin, 1- and 2-aminonaphthalene, p,p'-diaminostilbenes, pyrenes, quaternary phenanthridine salts, 9-aminoacridines, p,p'-diaminobenzophenone imines, anthracenes, oxacarbocyanine, merocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidazolylphenylamine, 2-oxo-3-chromen, indole, xanthen, 7-hydroxycoumarin, phenoxazine, calicylate, strophanthidin, porphyrins, triarylmethanes, flavin and many others. Many fluorescent tags are commercially available from various commercial sources, including Sigma Chemical Co. (St. Louis, Mo.), Molecular Probes, R&D systems (Minneapolis, Minn.), Pharmacia LKB Biotechnology (Piscataway, N.J.), Clontech Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), and Applied Biosystems (Foster City, Calif.).

The following non-limiting examples are intended to further illustrate embodiments of the invention.

EXAMPLES

Figure 2:
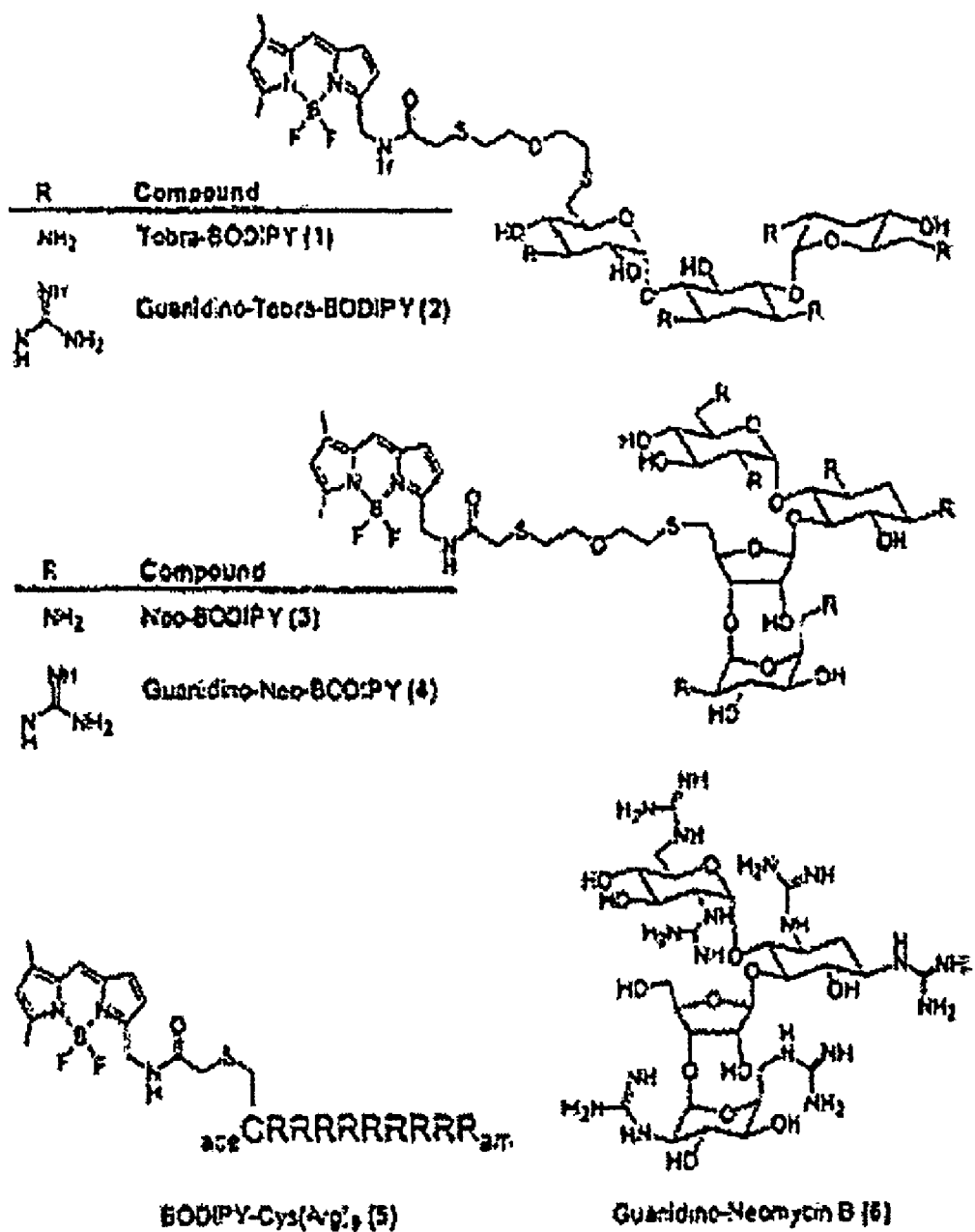
FIG. 2 illustrates the structures for the aminoglycosides and guanidinonoglycosides conjugates used to evaluate cellular uptake.

To examine how the cellular uptake of conjugated compounds is affected by guanidinylation, a series of BODIPY-tagged aminoglycosides and guanidinoglycosides were synthesized based upon tobramycin and neomycin B (see, e.g., FIG. 2). The fluorescence of BODIPY is relatively insensitive to changes in the local environment. By using fluorescein as a reference ($\phi$=0.93 at pH 9.0), the emission quantum efficiently ($\phi$) of all five BODIPY conjugates described below is equal to 1.0 at pH 7.5.

Example 1

Synthesis and Characterization of Tobra-BODIPY

A general scheme for synthesizing tobra-BODIPY is shown below (Scheme IV):

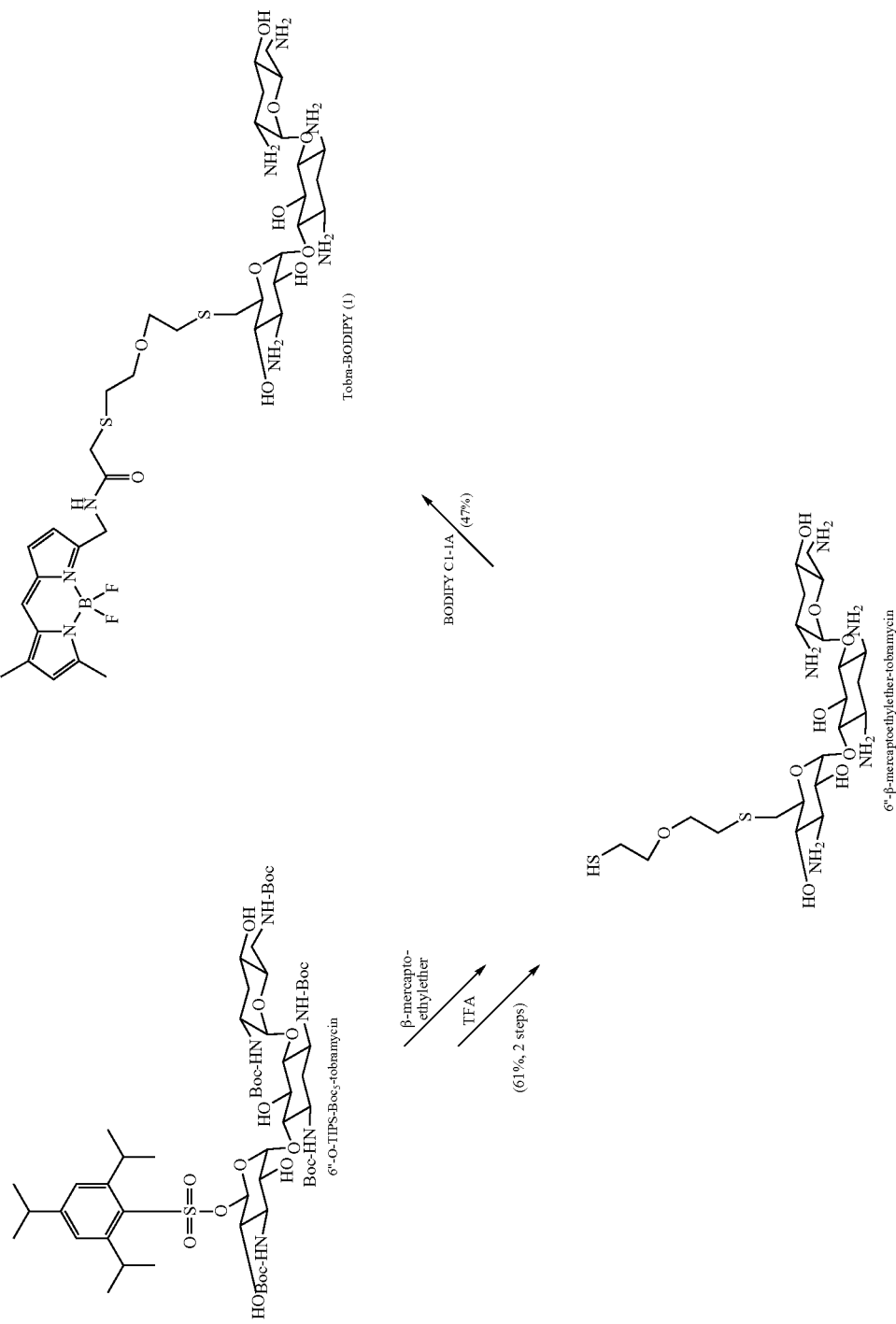

As a first step of the synthesis of tobra-BODIPY, 6"-O-TIPS-Boc$_5$-tobramycin was synthesized, as shown by the reaction Scheme V:

Scheme V
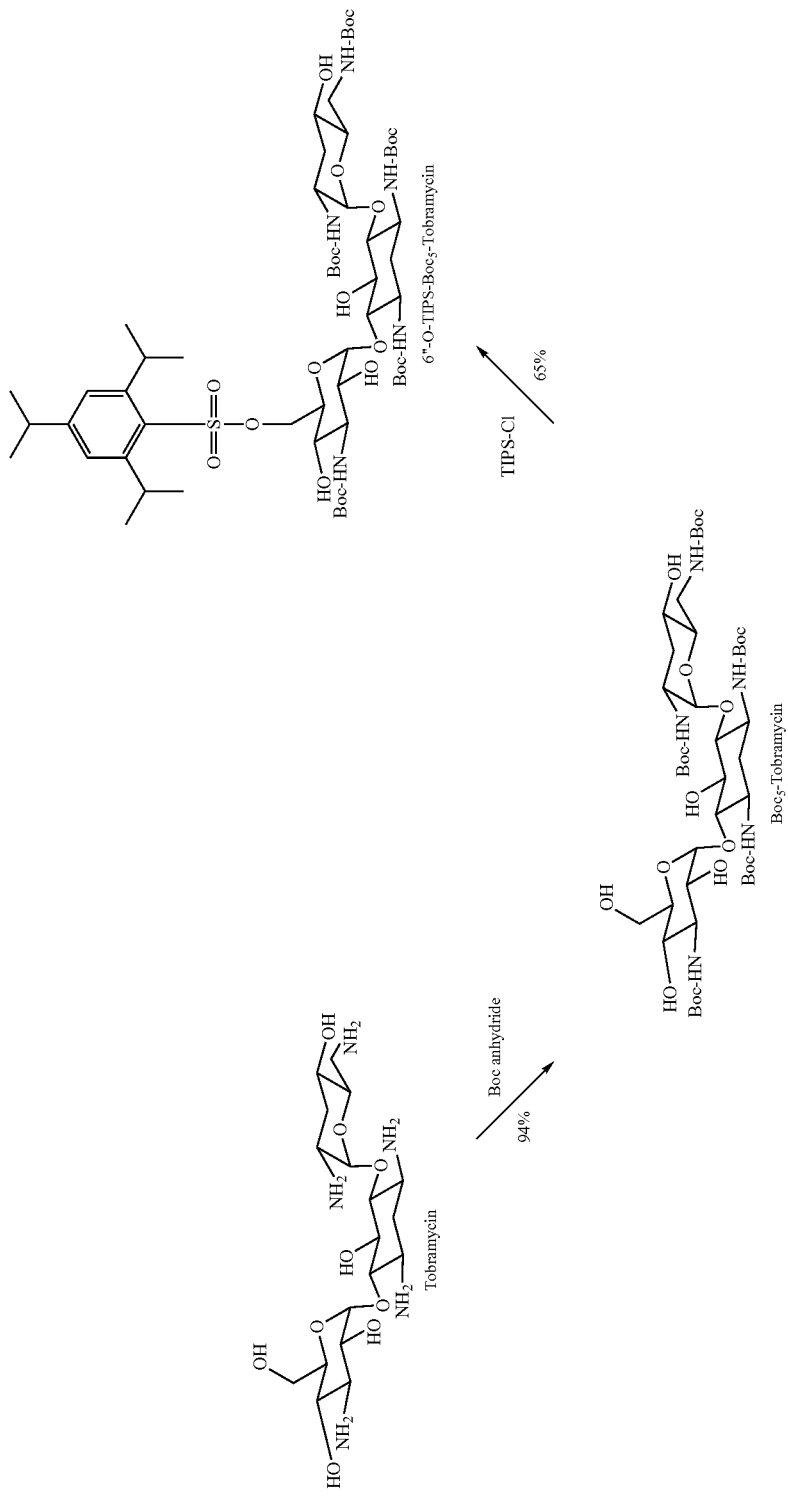

As shown by Scheme V, the first step of the synthesis of 6"-O-TIPS-Boc$_5$-tobramycin was the synthesis of Boc$_5$-tobramycin. To prepare Boc$_5$-tobramycin, a solution of tobramycin (0.5 g, 1.070 mmol) in 14 mL aqueous DMSO (DMSO:water=6:1) was treated with di-tert-butyldicarbonate (1.4 g, 6.420 mmol, 6.0 equiv). The solution was heated at 60° C. for 4 hours, then cooled to 23° C. A solution of 30% aqueous ammonia (5 mL) was added dropwise to the mixture. The precipitated solid was filtered, washed with water (3×200 mL), and dried in vacuo (970 mg, 94%): Rf 0.31, 7.5% methanol-dichloromethane; $^1$H NMR (500 MHz, methanol-$d_4$) δ 5.10 (br, 1H), δ 5.07 (br, 1H), δ 3.93 (m, 1H), δ 3.78 (m, 1H), δ 3.70 (m, 2H), δ 3.60 (m, 3H), δ 3.30-3.50 (m, 9H), δ 2.11 (m, 1H), δ 1.99 (m, 1H), δ 1.64 (q 1H, J=12.5 Hz), δ 1.42-1.48 (m, 46H); HRMS (FAB) m/z calcd for $C_{43}H_{77}NaN_5O_{19}$ [M+Na]+ 990.5110. found 990.5102.

To complete the synthesis of 6"-O-TIPS-Boc$_5$-tobramycin, a solution of Boc$_5$-tobramycin (0.3 g, 0.310 mmol) in pyridine (5 mL) was treated with 2,4,6-triisopropylbenzenesulfonyl chloride (0.66 g, 2.180 mmol, 7.0 equivalent). Boc$_5$-tobramycin was made as described above. The reaction mixture was stirred at 23° C. for 12 hours. It was neutralized by adding hydrochloric acid (1.0 N), and partitioned between water (300 mL) and ethyl acetate (600 mL). The aqueous layer was separated and extracted with ethyl acetate (2×250 mL). The combined organic layer was washed with brine, dried over Na$_2$SO$_4$, and concentrated in vacuum. Flash chromatography (2.3% methanol-dichloromethane) afforded the desired product as a white solid (240 mg, 65%): Rf 0.33, 7.5% methanol-dichloromethane; $^1$H NMR (500 MHz, methanol-$d_4$) δ 7.28 (s, 2H), δ 5.09 (br, 2H), δ 4.40 (m, 1H), δ 4.27 (m, 1H), δ 4.14 (m, 3H), δ 3.72 (t, 1H, J=10.4 Hz), δ 3.40-3.60 (m, 12H), δ 2.94 (m, 1H), δ 2.04 (m, 2H), δ 1.64 (q, 1H, J=12.0 Hz), δ 1.42-1.48 (m, 46H), δ 1.26 (m, 18H), HRMS (FAB) m/z calcd for $C_{58}H_{99}NaN_5O_{21}S$ [M+Na]+ 1256.6451. found 1256.6487.

Next, 6"-β-mercaptoethylether-tobramycin trifluoroacetic acid was synthesized. To synthesize 6"-β-mercaptoethylether-tobramycin trifluoroacetic acid, 6"-O-TIPS-Boc$_5$-tobramycin (40 mg, 32 μmoles) made as described above was stirred under argon, for 2 hours, at 30° C. together with Cs$_2$CO$_3$ (21 mg, 64 μmoles), dry dimethylformamide (3 mL), and 2-mercaptoethylether (34 μl, 274 μmoles, 8.6 equiv), followed by dilution with ethyl acetate (100 mL), washing with water (4×50 mL) and brine (50 mL), and drying over sodium sulfate. The organic layer was then concentrated under to an oil reduced pressure, and kept under a high vacuum for 40 min. The crude product was dissolved in CH$_2$Cl$_2$ (2 mL), 1,2-ethanedithiol (15 μL), triisopropysilane (15 μL), and trifluoroacetic acid (3 mL), and stirred at room temperature for 15 min. The product was then diluted with toluene (50 mL) and concentrated to a solid at 50° C. under reduced pressure. The dilution and concentration procedure was performed twice. The white solid was then dissolved in water (100 mL) and washed with CHCl$_3$ (4×50 mL). The aqueous layer was concentrated under reduced pressure and twice lyophilized from 0.1% TFA (3 mL in water) to yield 25 mg of a white powder (61% yield, two steps). $^1$H-NMR (400 MHz, D$_2$O) δ 5.59 (d, J=3.6 Hz, 1H), δ 4.85 (d, J=4.0 Hz, 1H), δ 3.3-3.8 (m, 17H), δ 3.05 (d, d J$_1$=13.6 Hz, J$_2$=7.2 Hz, 1H), δ 2.94 (d, d J$_1$=11.6 Hz, J$_2$=2.4 Hz, 1H), δ 2.65-2.71 (m, 3H), δ 2.57 (t, J=6.4 Hz, 2H), δ 2.40 (d, t J$_1$=12.8 Hz, J$_2$=4.0 Hz, 1H), δ 2.14 (d, t J$_1$=12.4 Hz, J$_2$=4.4 Hz, 1H), δ 1.87 (q, J=11.2 Hz, 1H), δ 1.78 (q, J=12.8 Hz, 1H). ESI MS calculated for $C_{22}H_{45}N_5O_9S_2$: 587.3. found 588.2 [M+H]$^+$.

The final product, tobra-BODIPY hydrochloride, shown as (1) on Scheme IV was then synthesized. 6"-β-mercaptoethylether-tobramycin trifluoroacetic acid made as described above (5 mg, 4.3 μmoles) was dissolved in a degassed aqueous buffer (1 mL of 150 mM NaCl, 10 mM sodium phosphate pH 7.5, Ar sparged). Separately, BODIPY Cl-IA (2.5 mg, 6 μmoles, 1.4 equivalent Molecular Probes) was dissolved in dimethylsulfoxide (0.75 mL), and added, dropwise, to the tobramycin solution. The reaction was kept in the dark for 2 hours at room temperature, then diluted with water (8 mL) and loaded onto an activated C-18 reversed-phase cartridge (Waters, Sep-pack). The column was activated with 10 mL acetonitrile, 10 mL of water, the crude reaction was then loaded, washed with 1M NaCl (5 mL) and pure water (5 mL), then a 0-30% acetonitrile/water gradient was applied, and the fractions between 5-15% acetonitrile/water were collected and lyophilized to yield 2.2 mg (47%) of a red powder. All BODIPY-glycoside conjugates are slightly to moderately hygroscopic, therefore the absorption at 502 nm of each compound (in methanol) is used to confirm the yield of the conjugation reaction (taking ε502 nm=76,000 cm$^{-1}$ M$^{-1}$). $^1$H-NMR (400 MHz, D$_2$O) δ 7.39 (s, 1H), δ 6.91 (d, J=4.0 Hz, 1H), δ 6.30 (d, J=4.0 Hz, 1H), δ 6.22 (s, 1H), δ 5.55 (d, J=3.6 Hz, 1H), δ 4.94 (d, J=4.0 Hz, 1H), δ 4.49 (s, 2H), δ 3.25-3.90 (m, 19H), δ 3.05 (d, d J$_1$=13.6 Hz, J$_2$=7.2 Hz, 1H), δ 2.93 (d, d J$_1$=11.6 Hz, J$_2$=2.4 Hz, 1H), δ 2.60-2.67 (m, 5H), δ 2.40 (s, 3H), δ 2.29 (d, t J$_1$=12.4 Hz, J$_2$=3.6 Hz, 1H), δ 2.10-2.14 (m, 4H), δ 1.84 (q, J=11.6 Hz, 1H), δ 1.66 (q, J=12.8 Hz, 1H). MALDI TOF MS calculated for $C_{36}H_{59}BF_2N_8O_{10}S_2$: 876.3. found 877.4 [M+H]$^+$. found 899.3 [M+Na]$^+$. found 915.4 [M+K]$^+$.

Example 2

Synthesis and Characterization of Guanidino-Tobra-BODIPY

A scheme for synthesizing guanidino-tobra-BODIPY is shown below (Scheme

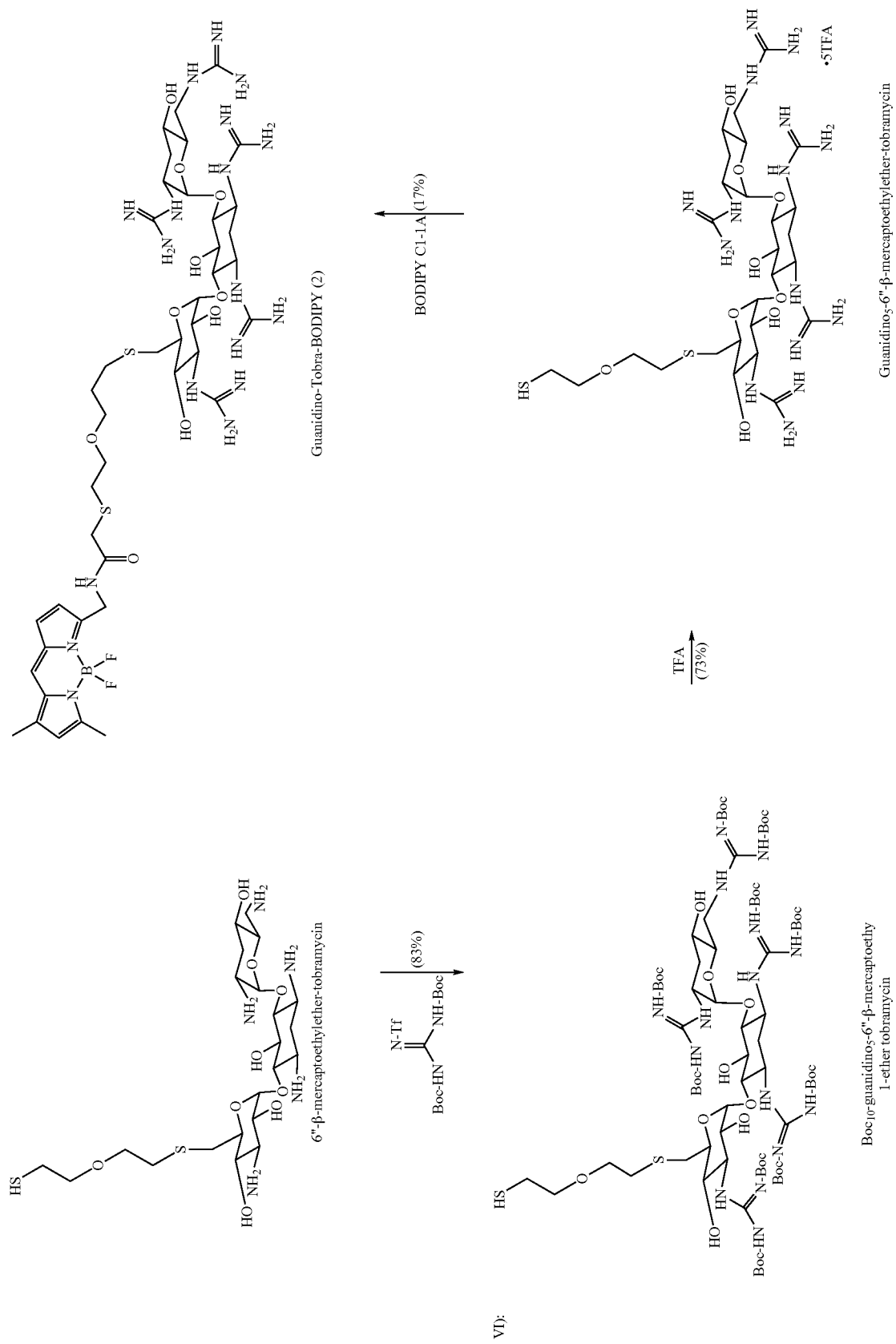

As shown by Scheme VI, the first step of the synthesis of guanidino-tobra-BODIPY was the synthesis of $Boc_{10}$-guanidino$_5$-6"-β-mercaptoethylether-tobramycin. To prepare $Boc_{10}$-guanidino$_5$-6"-β-mercaptoethylether-tobramycin, 6"-β-mercaptoethylether tobramycin trifluoroacetic acid made as described in Example 1 (70 mg, 60 µmoles), was dissolved in methanol (4 mL) and treated with N,N'-di-Boc-N"-trifylguanidine (420 mg, 1.08 mmoles, 17.9 equivalent), dithiothreitol (42 mg, 272 µmoles), and triethylamine (210 µL, 1.5 mmoles, 25 equivalent) for 26 hours at room temperature under argon. The product was then diluted by 150 mL of $CHCl_3$ and washed with 0.1M citric acid (three times, 50 mL each time) and brine (50 mL), then dried over sodium sulfate. The organic layer was concentrated to a solid and purified on silica gel using flash chromatography and 0-2% methanol in $CH_2Cl_2$ to afford 90 mg of an off-white solid (83% yield). $^1$H-NMR (400 MHz, $CDCl_3$) δ 11.50 (s, 1H), δ 11.47 (s, overlapping, 2H), δ 11.45 (s, 1H), δ 11.38 (s, 1H), δ 8.86 (d, J=3.6 Hz, 1H), δ 8.55 (d, J=9.0 Hz, 1H), δ 8.46 (t, J=6.3 Hz, 1H), δ 8.17 (d, J=8.7 Hz, 1H), δ 5.30-5.40 (m, 2H), δ 4.97 (d, J=3.9 Hz, 1H), δ 4.02 (br d, d $J_1$=12 Hz, $J_2$=8.4 Hz, 1H), δ 3.78-3.94 (m, 2H), δ 3.31-3.72 (m, 10H), δ 3.18 (br d, $J_1$=11.4 Hz, 2H), δ 2.95-3.03 (m, 2H), δ 2.61-2.73 (m, 8H), δ 2.36 (s, 1H), δ 2.02 (s, 1H), δ 1.93 (s, 1H), δ 1.62-1.69 (m, 18H), δ 1.42-1.51 (m, 18H), δ 1.28 (s, 1H). ESI MS calculated for $C_{77}H_{135}N_{15}O_{29}S_2$: 1797.8. found 1798.3 $[M+H]^+$. found 899.7 $[M+2H]^{2+}$.

Guanidino$_5$-6"-β-mercaptoethylether-tobramycin trifluoroacetic acid was then prepared by dissolving $Boc_{10}$-guamidino$_5$-6"-β-mercaptoethyelther-tobramycin (41 mg, 23 µmoles) in $CHCl_3$ (1 mL) and treating the solution with triisopropysilane (30 µL, 146 µmoles), 1,2-ethanedithiol (30 µL, 358 µmoles), and trifluoroacetic acid (1.5 mL) for 3 hours at room temperature. The product was then diluted with water (100 mL) and washed with $CHCl_3$ (twice, 30 mL each time) and diethyl ether (twice, 30 mL each time). The aqueous layer was concentrated to a solid under vacuum, then dissolved in 0.1% trifluoroacetic acid in water (2 mL) and lyophilized to yield 22 mg of a white solid (73% yield). $^1$H-NMR (400 MHz, $d_6$-MeOD) δ 5.65 (d, J=3.6 Hz, 1H), δ 5.06 (d, J=3.6 Hz, 1H), δ 4.10 (t, J=6.4 Hz, 1H), δ 3.45-3.88 (m, 17H), δ 3.04 (d, d $J_1$=13.6 Hz, $J_2$=2.8 Hz, 1H), δ 2.62-2.78 (m, 5H), δ 2.11-2.19 (m, 2H), δ 1.68-1.78 (m, 2H). MALDI TOF MS calculated for $C_{27}H_{55}N_{15}O_9S_2$: 797.37. found 820.32 $[M+Na]^+$.

The final product, guainidino-tobra-BODIPY hydrochloride shown as (2) on Scheme VI was then synthesized. Guanidino$_5$-6"-β-mercaptoethylether-tobramycin trifuoroacetic acid obtained as described above (10 mg, 4.3 µmoles) was added to an aqueous degassed buffer (2 mL of 50 mM sodium phosphate pH 7.5, Ar sparged). Separately, BODIPY Cl-IA (2.5 mg, 6 µmoles, 1.4 equivalent, Molecular Probes) was dissolved in dimethylsulfoxide (0.75 mL), and added, dropwise, to the tobramycin solution. The resulting precipitation of guanidino-tobramycin was partially reversed upon addition of NaCl (150 mM final concentration). The reaction was then kept in the dark for 2 hours at room temperature and diluted into 5% acetonitrile in water (15 mL; containing 100 mM NaCl) and loaded onto an activated C-18 reversed-phase cartridge (Waters, Sep-pack). The column was then washed with 5 mL of water and the product was eluted with 25% acetonitrile/water and lyophilized to yield 1.3 mg (17% yield) of a red powder. All BODIPY-glycoside conjugates are slightly to moderately hygroscopic, the absorption at 502 nm (in methanol) was used to calculate the yield of the conjugation reaction (taking ε502 nm=76,000 $cm^{-1}$ $M^{-1}$). The low yield of this particular reaction was attributed to the solubility problems of the guanidino-tobramycin starting material in 50 mM phosphate/25% DMSO in water (its solubility in 10 mM sodium phosphate pH 7.5, 250 mM NaCl, 25% DMSO is, however, significantly better). $^1$H-NMR (400 MHz, $D_2O$) δ 7.41 (s, 1H), δ 6.92 (d, J=3.6 Hz, 1H), δ 6.31 (d, J=3.6 Hz, 1H), δ 6.24 (s, 1H), δ 5.40 (d, J=3.6 Hz, 1H), δ 4.98 (s, 1H), δ 4.51 (s, 2H), δ 4.03 (t, J=6.8 Hz, 1H), δ 3.79 (t, J=8.4 Hz, 1H), δ 3.27-3.64 (m, 18H), δ 2.90 (d, J=13.2 Hz, 1H), δ 2.55-2.67 (m, 5H), δ 2.41 (s, 3H), δ 2.02-2.15 (m, 5H), δ 1.54-1.62 (m, 2H). MALDI TOF calculated for $C_{41}H_{69}BF_2N_{18}O_{10}S_2$: 1086.49. found 1087.36 $[M+H]^+$. found 1109.30 $[M+Na]^+$.

Example 3

Synthesis and Characterization of Neo-BODIPY

A scheme for synthesizing neo-BODIPY is shown below (Scheme VII):

As shown by Scheme VII, the first step of the synthesis of neo-BODIPY was the synthesis of 5"-O-TIPS-$Boc_6$-neomycin B. To prepare 5"-O-TIPS-$Boc_6$-neomycin B, Scheme VII
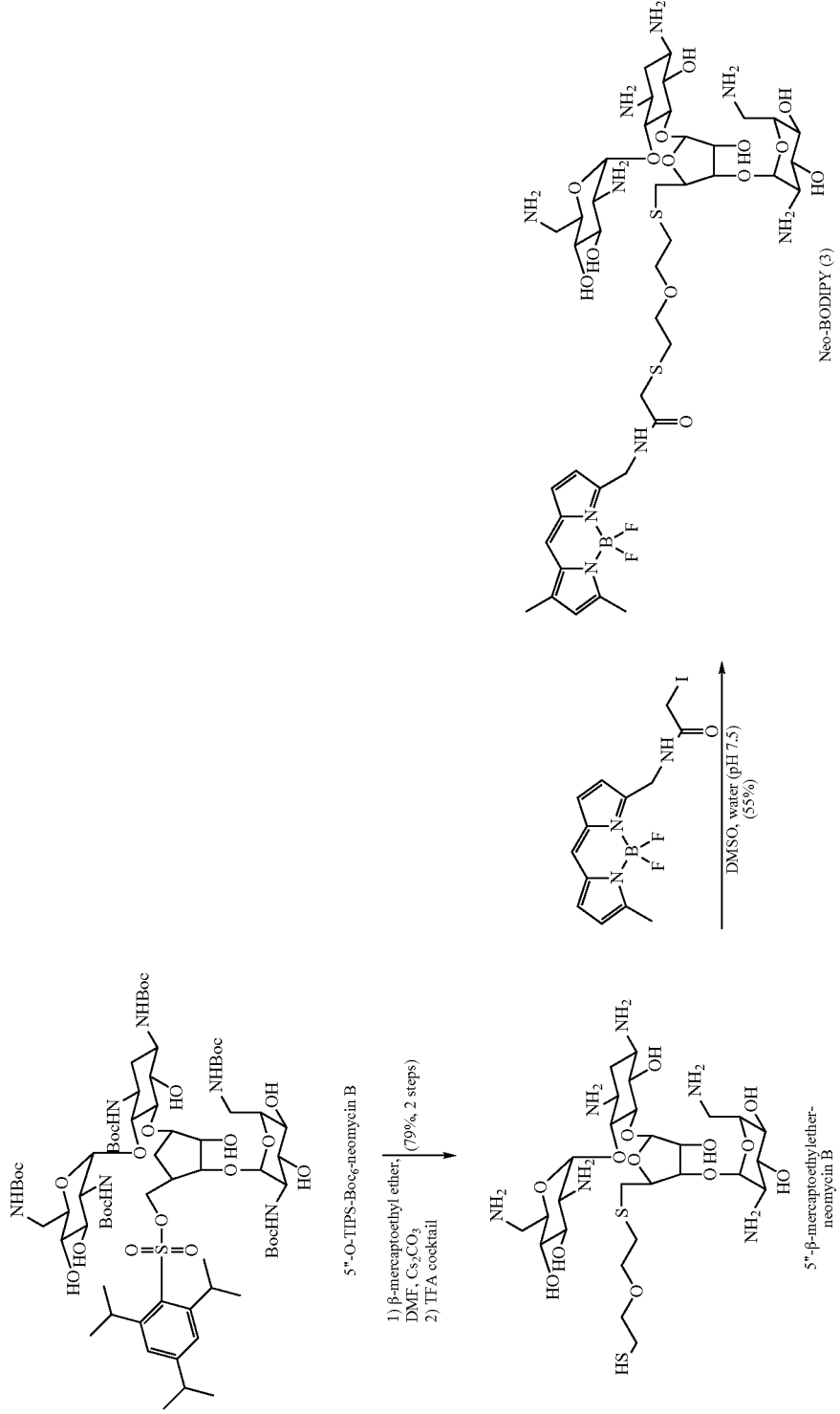

a reaction Scheme VIII was used:

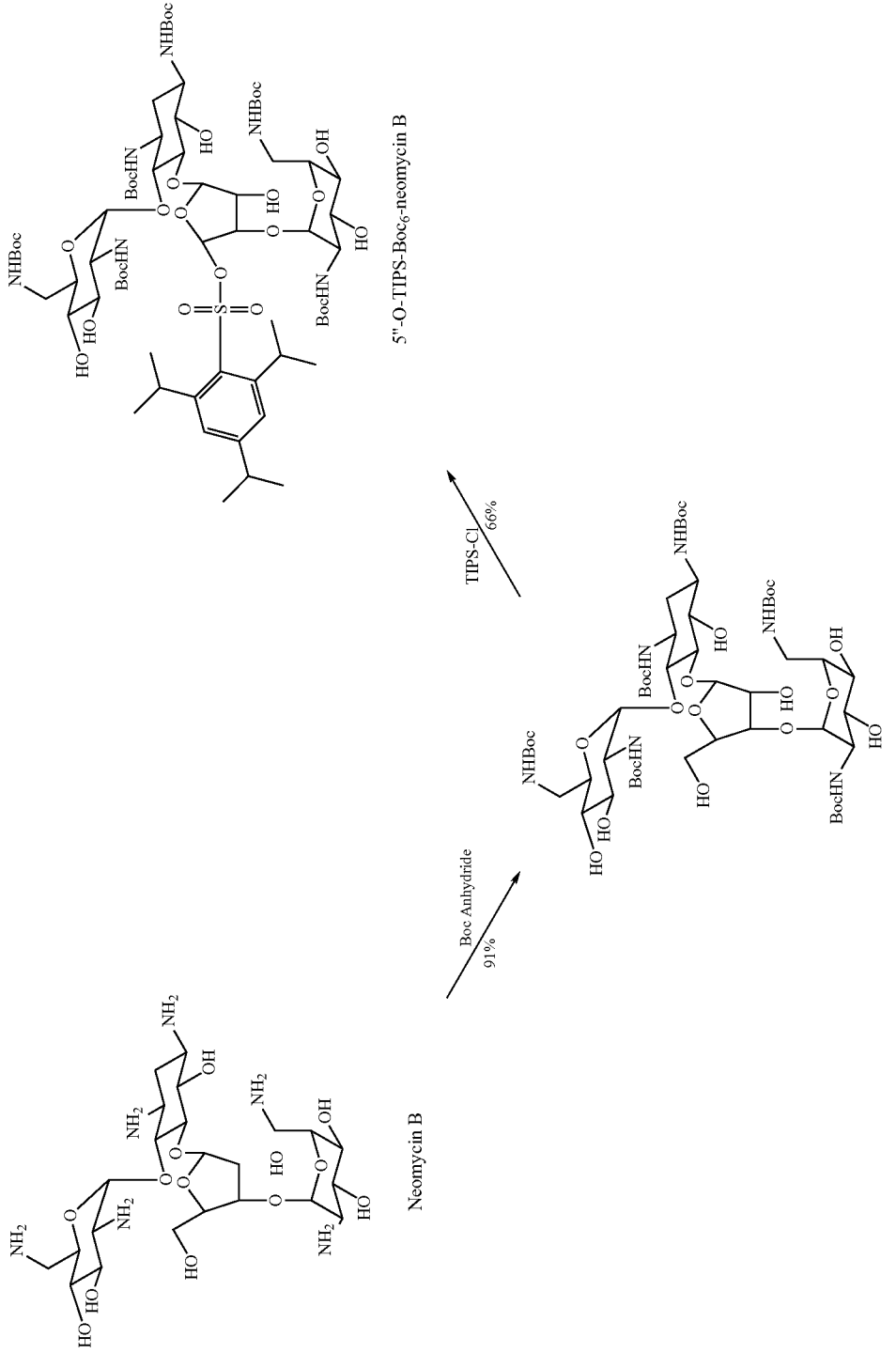

As shown by Scheme VIII, to prepare 5"-O-TIPS-Boc$_6$-neomycin B. Boc$_6$-neomycin B was made first. To prepare Boc$_6$-neomycin B, a solution of neomycin B (1.0 g, 1.626 mmol) in a mixture of diethylformamide (20 mL), water (4 mL) and triethylamine (2 mL) was treated with di-tert-butyl-carbonate (2.1 g, 9.756 mmol, 6.0 equivalent). The reaction solution was heated to 60° C. for 5 hours, then cooled to 23° C. The volatile compounds were removed in vacuum. The residue was partitioned between water (300 mL) and ethyl acetate (600 mL). The aqueous layer was separated and extracted with ethyl acetate (twice, 250 mL each time). The combined organic layer was washed with brine, dried over Na$_2$SO$_4$, and concentrated in vacuum. Flash column chromatography (4.3% methanol-dichloromethane) afforded the desired product as a white solid (1.8 g, 91%): Rf 0.36, 10% methanol-dichloromethane; $^1$H NMR (500 MHz, methanol-$_{d4}$) δ 5.28 (br, 1H), δ 5.16 (s, 1H), δ 4.90 (s, 1H), δ 4.18 (s, 1H), δ 3.96 (s, 1H), δ 3.82-3.90 (m, 3H), δ 3.76 (s, 1H), δ 3.64-3.72 (m, 4H), δ 3.48 (m, 6H), δ 3.19-3.30 (m, 5H), δ 1.94 (m, 1H). δ 1.56 (m, 1H), δ 1.38-1.46 (m, 54H); HRMS (FAB) m/z calcd for C$_{54}$H$_{94}$NaN$_6$O$_{25}$ [M+Na]+ 1237.6166. found 1237.6141.

Boc$_6$-neomycin B prepared as described above was then used to synthesize 5"-O-TIPS-Boc$_6$-neomycin B. A solution of Boc$_6$-neomycin B (1.0 g, 0.823 mmol) in pyridine (20 mL) was treated with 2,4,6-triisopropylbenzenesulfonyl chloride (8 g, 26.4 mmol, 32.0 equivalent). The reaction mixture was stirred at 23° C. for 12 hours. It was neutralized by adding hydrochloric acid (1.0 N) and partitioned between water (300 mL) and ethyl acetate (600 mL). The aqueous layer was separated and extracted with ethyl acetate (twice, 250 mL each time). The combined organic layer was washed with brine, dried over Na$_2$SO$_4$, and concentrated in vacuum. Flash chromatography (3.3% methanol-dichloromethane) afforded the desired product as a white solid (0.8 g, 66%): Rf 0.40, 10% methanol-dichloromethane; $^1$H NMR (500 MHz, methanol-$_{d4}$) δ 7.32 (2, 2H), δ 5.45 (br, 1H), δ 5.18 (br, 1H), δ 4.60 (br, 1H), δ 4.25 (m, 1H), δ 4.26 (m, 2H), δ 4.15 (m, 4H), δ 3.88 (s, 1H), δ 3.78 (m, 1H), δ 3.73 (m, 2H), δ 3.60 (m, 1H), δ 3.50 (m, 4H), δ 3.36-3.42 (m, 4H), δ 3.20 (m, 2H), δ 2.96 (m, 1H), δ 1.95 (m, 1H), δ 1.56 (m, 1H), δ 1.38-1.46 (m, 54H), δ 1.27 (m, 18H); HRMS (FAB) m/z calcd for C$_{68}$H$_{116}$NaN$_6$O$_{27}$S [M+Na]+ 1503.7507. found 1503.7498.

5"-O-TIPS-Boc$_6$-neomycin B prepared as described above was then used to synthesize 5"-β-mercaptoethylether-neomycin trifluoroacetic acid. 5"-O-TIPS-Boc$_6$-neomycin B (40 mg, 27 μmoles) was dissolved in dimethylformamide (1.5 mL) and treated with Cs$_2$CO$_3$ (100 mg, 307 μmoles) and 2-mercaptoethylether (125 μL, 1 mmoles, 37 equiv). The reaction was kept under argon for 7 hours at 30° C., and the product was diluted with ethyl acetate (150 mL), washed with 0.1 M citric acid (50 mL), water (three times, 50 mL each time), brine (50 mL), and dried over sodium sulfate. The organic layer was concentrated under reduced pressure and kept under a high vacuum overnight. The crude product was dissolved in CH$_2$Cl$_2$ (4 mL) and treated with 1,2-ethanedithiol (20 μL), triisopropysilane (20 μL), and trifluoroacetic acid (5 mL) for 15 min. at room temperature. The product was diluted with toluene (50 mL), concentrated under vacuum at 50° C. (twice) and kept under high-vacuum for 6 hours. The solid was then dissolved in 0.1% trifluoroacetic acid in water (3 mL), filtered through glass wool, and lyophilized to afford 30 mg of a white solid (79% yield, two steps). $^1$H-NMR (400 MHz, D$_2$O) δ 5.88 (d, J=4.0 Hz, 1H), δ 5.23 (d, J=3.2 Hz, 1H), δ 5.12 (s, 1H), δ 4.21-4.24 (m, 2H), δ 4.13-4.18 (m, 2H), δ 4.04 (s, 1H), δ 3.91 (t, J=10 Hz, 1H), δ 3.82 (t, J=9.6 Hz, 1H), δ 3.71-3.75 (m, 2H), δ 3.64 (s, 1H), δ 3.48-3.57 (m, 4H), δ 3.17-3.41 (m, 8H), δ 3.11 (d, d J$_1$=13.6 Hz, J$_2$=9.6 Hz, 1H), δ 2.97 (d, d J=13.2 Hz, J$_2$=3.6 Hz, 1H), δ 2.65-2.74 (m, 4H), δ 2.55 (t, J=6.0 Hz, 2H), δ 2.30 (d, t J$_1$=12.4 Hz, J$_2$=4.4 Hz, 1H), δ 1.71 (q, J=12.4 Hz, 1H). ESI MS calculated for C$_{27}$H$_{54}$N$_6$O$_{13}$S$_2$: 734.3. found 735.3 [M+H]+.

5"-β-mercaptoethylether-neomycin trifluoroacetic acid prepared as described above was then used to synthesize the final product, neo-BODIPY hydrochloride, shown as (3) on Scheme VII. 5"-β-mercaptoethylether-neomycin B trifluoroacetic acid (10 mg, 7 μmoles), was dissolved in an aqueous buffer (15 mL of 10 mM sodium phosphate, 150 mM NaCl, pH 7.5, Ar sparged). Separately, BODIPY C1-IA (1.8 mg, 4.3 μmoles, 0.61 equivalent, Molecular Probes) was dissolved in diimethylsulfoxide (1.5 mL), and added, dropwise, to the neomycin solution and allowed to react in the dark for 2 hours at room temperature. The product was then diluted with water (8 mL) and loaded onto an activated C-18 reversed-phase cartridge (Waters, Sep-pack), the column was then washed with 5% acetonitrile (5 mL, containing 100 mM NaCl in water) and then pure water (1 mL). The product eluted between 0-15% acetonitrile (in water) and was lyophilized to yield 2.9 mg (55% yield) of a red powder. All BODIPY-glycoside conjugates are slightly to moderately hygroscopic, therefore the absorption at 502 nm of each compound (in methanol) is used to confirm the yield of the conjugation reaction (taking ε502 nm=76,000 cm$^{-1}$ M$^{-1}$). $^1$H-NMR (400 MHz, D$_2$O) δ 7.41 (s, 1H), δ 6.92 (d, J=4.0 Hz, 1H), δ 6.30 (d, J=4.0 Hz, 1H), δ 6.24 (s, 1H), δ 5.89 (d, J=4.0 Hz, 1H), δ 5.27 (d, J=3.6 Hz, 1H), δ 5.15 (s, 1H), δ 4.50 (s, 2H), δ 4.26-4.32 (m, 2H), δ 4.21 (p, J=4.0 Hz, 1H), δ 4.15 (t, J=4.4 Hz, 1H), δ 4.07 (t, J=3.2 Hz, 1H), δ 3.83-3.88 (m, 3H), δ 3.77 (t, J=9.2 Hz, 1H), δ 3.67 (s, 1H), δ 3.53-3.59 (m, 4H), δ 3.45 (s, 1H), δ 3.40 (d, d J=11.2 Hz, J$_2$=4.0 Hz, 1H), δ 3.67 (s, 1H), δ 3.20-3.35 (m, 5H), δ 3.09 (d d, J=13.2 Hz, J$_2$=7.6 Hz, 1H), δ 2.98 (d d, J=13.6 Hz, J$_2$=4.4 Hz, 1H), δ 2.67-2.77 (m, 5H), δ 2.41 (s, 3H), δ 2.25 (d t, J$_1$=12.4 Hz, J$_2$=4.4 Hz, 1H), δ 2.15 (s, 3H), δ 1.65 (q, J=12.8 Hz, 1H). MALDI TOF MS calculated for C$_{41}$H$_{68}$BF$_2$N$_9$O$_{14}$S$_2$: 1023.44, observed 1024.42 [M+H]+, observed 1046.43 [M+Na]+, observed 1062.54 [M+K]+.

Example 4

Synthesis and Characterization of Guanidine-neo-BODIPY

A scheme for synthesizing guanidino-neo-BODIPY is shown below (Scheme IX):

Scheme IX
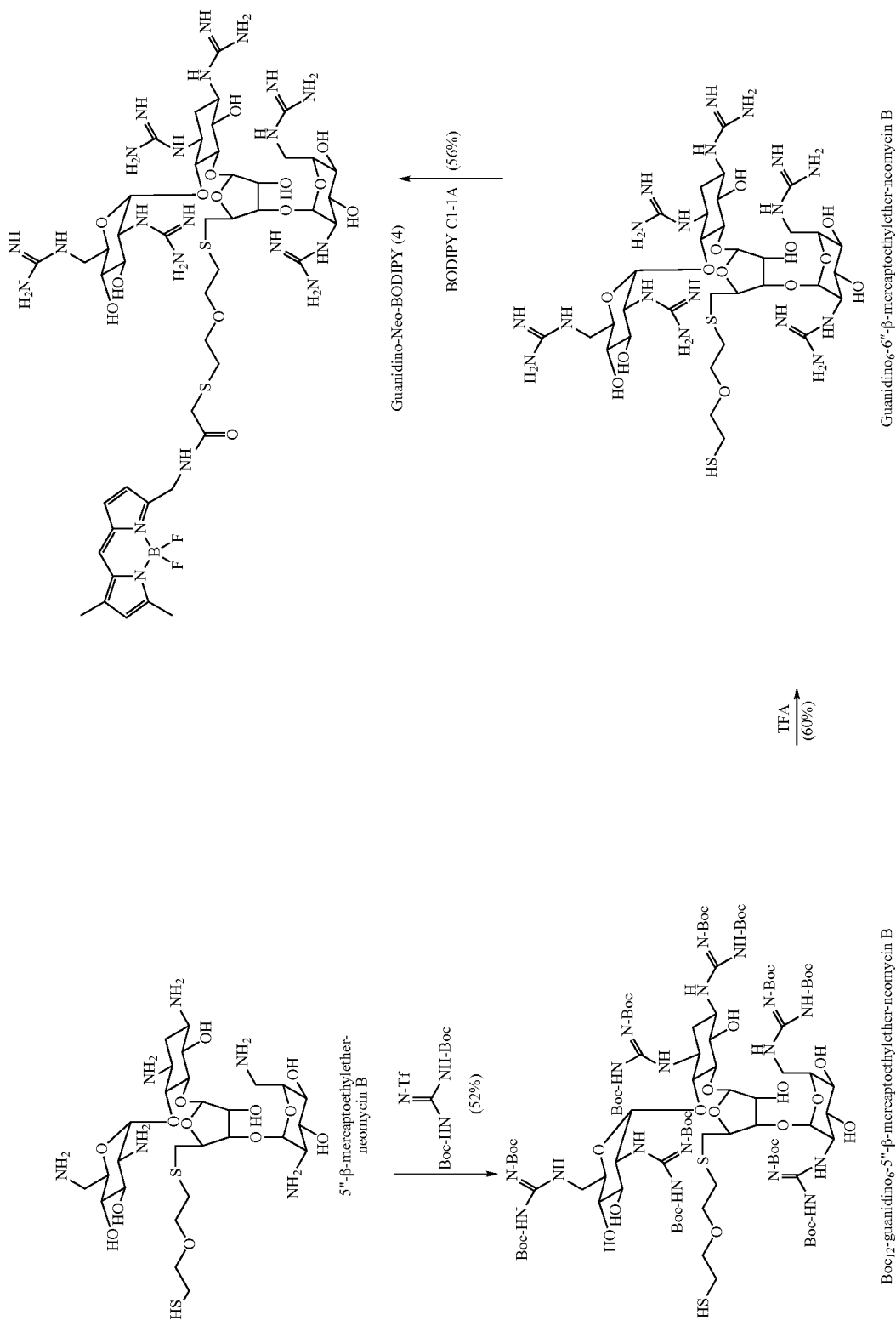

To prepare guanidino-neo-BODIPY, $Boc_{12}$-guanidino$_6$-5"-β-mercaptoethylether-neomycin B was made first. To prepare $Boc_{12}$-guanidino$_6$-5"-β-mercaptoethylether-neomycin B, 5"-β-mercaptoethylether-neomycin B trifluoroacetate synthesized as described in Example 3 (90 mg, 63 µmoles), was dissolved in methanol (5 mL), $CHCl_3$ (3 mL), and treated with N,N'-di-Boc-N"-triflylguanidine (530 mg, 1.35 mmoles, 21 equivalent), dithiothreitol (50 mg, 324 µmoles), and triethylamine (530 mL, 3.8 mmoles, 60 eqiv.) for 96 hours at room temperature under argon. The product was then diluted with $CHCl_3$ (200 mL) and washed twice with 0.1 M citric acid (100 mL each time), brine (50 mL) and dried over sodium sulfate. The organic layer was then concentrated to a solid under reduced pressure and purified on silica gel using flash chromatography (0-1% methanol in $CHCl_3$ to afford 71 mg of an off-white solid (52% yield). $^1$H-NMR (300 MHz, $CDCl_3$) δ 11.41 (s, 2H, overlapping), δ 11.40 (s, 1H), δ 11.38 (s, 1H), δ 11.33 (s, 1H), δ 11.30 (s, 1H), δ 9.34 (d, J=8.1 Hz, 1H), δ 8.92 (d, J=7.2 Hz, 1H), δ 8.47 (t, J=5.4 Hz, 1H), δ 8.41 (t, J=5.4 Hz, 1H), δ 8.34 (d, J=6.6 Hz, 1H), δ 8.18 (d, J=9.0 Hz, 1H), δ 5.94 (d, J=4.4 Hz, 1H), δ 5.62 (d, J=4.2 Hz, 1H), δ 5.01 (d, J=4.8 Hz, 1H), δ 4.91-4.94 (m, 2H), δ 4.38-4.95 (m, 3H), 4.05-4.22 (m, 4H), δ 3.79-3.92 (m, 3H), δ 3.66-3.74 (m, 2H), δ 3.55-3.59 (m, 4H), δ 3.25-3.42 (m, 4H), a 2.54-2.74 (m, 5H), δ 2.44 (d t, J=12.4 Hz, $J_2$=4.4 Hz, 1H), δ 1.22-1.60 (m, 109H). ESI MS calculated for $C_{94}H_{163}N_{17}O_{37}S_2$: 2186.1. found 1094.2 $[M+2H]^{2+}$.

Using $Boc_{12}$-guanidino$_6$-5"-β-mercaptoethylether-neomycin B made as described above, guanidino$_6$-5"-β-mercaptoethylether-neomycin B trifluoroacetic acid was then made. $Boc_2$-guanidino$_6$-5"-β-mercaptoethylether-neomycin B (65 mg, 30 µmoles) was dissolved in $CHCl_3$ (1.5 mL) and treated with triisopropylsilane (80 µL, 390 µmoles), 1,2-ethanedithiol (30 µL, 955 µmoles), and trifluoroacetic acid (3 mL) for 3 hours at room temperature. The product was then diluted into water (200 mL) and washed twice with $CHCl_3$ (100 mL each time) and twice with diethyl ether (50 mL each time). The aqueous layer was then concentrated to a solid under reduced pressure, dissolved in 0.1% trifluoroacetic acid in water (2 mL) and lyophilized to yield 30 mg of a white solid (60% yield). $^1$H-NMR (400 MHz, $D_2O$) δ 5.83 (d, J=3.2 Hz, 1H), δ 5.05 (s, 1H), δ 4.94 (s, 1H), δ 4.23-4.26 (m, 2H), δ 3.93-4.03 (m, 3H), δ 3.25-3.69 (m, 20H), δ 2.87 (d, d $J_1$=14.4 Hz, $J_2$=4.4 Hz, 1H), δ 2.55-2.67 (m, 5H), δ 2.08 (d t, $J_1$=12.0 Hz, $J_2$=4.4 Hz, 1H), δ 1.71 (q, J=12.0 Hz, 1H). MALDI TOF MS calculated for $C_{33}H_{66}N_{18}O_{13}S_2$: 986.45. found 987.49 $[M+H]^+$.

The final product, guanidino-Neo-BODIPY hydrochloride, shown as (4) on Scheme IX was then synthesized. Guanidino$_6$-5"-β-mercaptoethylether-neomycin B trifluoroacetic acid made as described above (9 mg, 5.4 µmoles) was dissolved in an aqueous buffer (3.0 mL of 10 mM sodium phosphate pH 7.5, 150 mM NaCl, Ar sparged). Separately BODIPY Cl-IA (1.7 mg, 4.1 µmoles, 0.76 equivalent, Molecular Probes) was dissolved in DMSO (1.5 mL), and added, dropwise, to the neomycin solution and allowed to react in the dark for 2 hours at room temperature. The product was then diluted with water (8 mL) and loaded onto an activated C-18 reversed-phase cartridge (Waters, Sep-pack). The column was washed with 5% acetonitrile (5 mL containing 100 mM NaCl in water) and pure water (1 mL). The product eluted between 0-20% acetonitrile (in water), and was lyophilized to yield 4.5 mg (56% yield) of a red powder. All BODIPY-glycoside conjugates are slightly to moderately hygroscopic, therefore the absorption at 502 nm of each compound (in methanol) is used to confirm the yield of the conjugation reaction (taking ε502 nm=76,000 $cm^{-1}$ $M^{-1}$). $^1$H-NMR (400 MHz, $D_2O$) δ 7.40 (s, 1H), δ 6.92 (d, J=4.0 Hz, 1H), δ 6.31 (d, J=4.0 Hz, 1H), δ 6.24 (s, 1H), δ 5.84 (d, J=3.6 Hz, 1H), δ 5.07 (s, 1H), δ 4.91 (s, 1H), δ 4.51 (s, 2H), δ 4.21-4.24 (m, 2H), δ 3.93-4.00 (m, 3H), δ 3.80 (t, J=8.4 Hz, 1H), δ 3.66-3.71 (m, 2H), δ 3.25-3.55 (m, 15H), δ 2.80 (d, d $J_1$=14.4 Hz, $J_2$=4.4 Hz, 1H), δ 2.50-2.67 (m, 6H), δ 2.41 (s, 3H), δ 2.15 (s, 3H), δ 2.08 (d t, $J_1$=12.0 Hz, $J_2$=4.4 Hz, 1H), δ 1.57 (q, J=12.0 Hz, 1H). MALDI TOF MS calculated for $C_{47}H_{80}BF_2N_{21}O_{14}S_2$: 1275.57. found 1276.57 $[M+H]^+$.

Example 5

Synthesis and Characterization of BODIPY-Cys(Arg)$_9$

A scheme for synthesizing BODIPY-Cys(Arg)$_9$ is shown below (Scheme X):

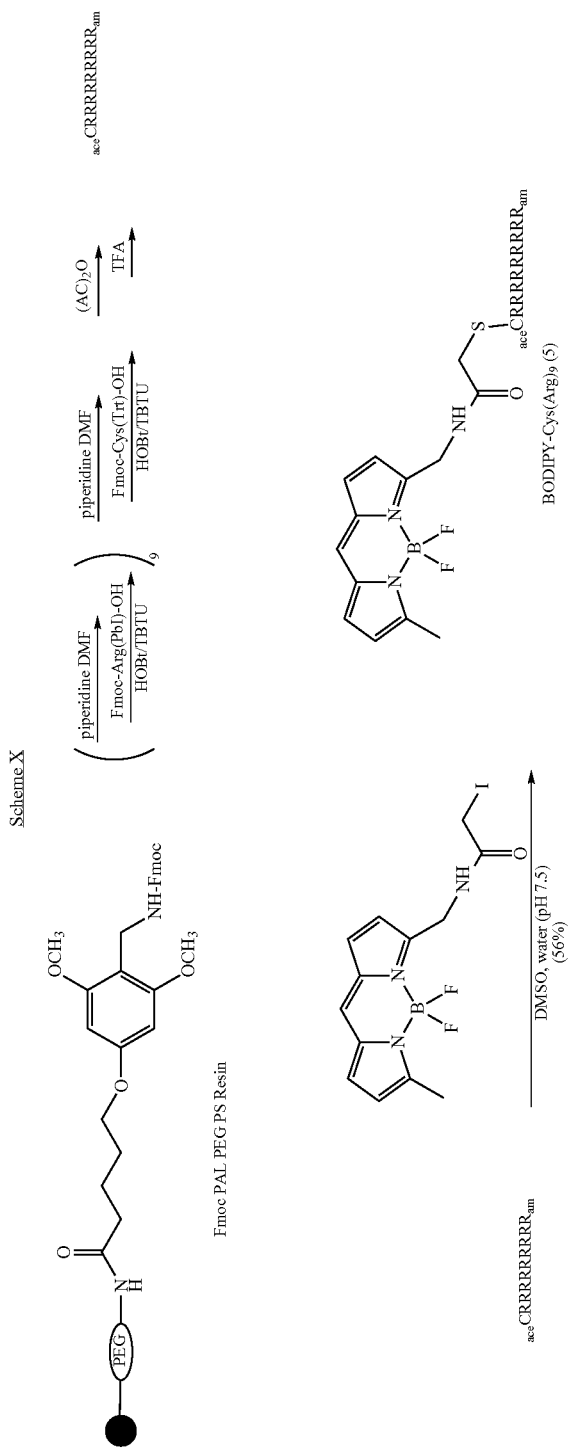

To synthesize BODIPY-Cys(Arg)$_9$, ace-CRRRRRRRPP-am trifluoroacetatic acid. To make ace-CRRRRRRR-am trifluoroacetatic acid, standard Fmoc solid-phase synthesis was used. Fmoc PAL PEG PS resin (1 g, 0.15 mmole, PerSeptive Biosystems), was de-protected using 20% piperidine in dimethylformamide for 20 minutes at room temperature, washed three times with dimethylformamide (7 mL each time), twice with diethyl ether (7 mL each time), and again three times with dimethylformamide (7 mL each time). The resin was then treated with TBTU (97 mg, 0.3 mmoles), Fmoc Arg (Pbf)-OH (195 mg, 0.3 mmoles), HOBt (46 mg, 0.3 mmoles), 2,4,6 collidine (0.4 mL, 3.0 mmoles), in DMF (7 mL), for at least 1 hour at room temperature on a shaker. The resin was then washed as above. The de-protection and coupling processes were repeated nine times total (as above). The final coupling reaction utilized Fmoc-Cys(Trt)-OH (264 mg, 0.45 mmoles), TBTU (145 mg, 0.45 mmoles), HOBt (46 mg, 0.45 mmoles), 2,4,6 collidine (0.6 mL, 4.5 mmoles), in DMF (7 mL) and lasted for 2 hours at room temperature on a shaker. Following de-protection and washes (as above), the terminus was acylated using HOBt (80 mg, 0.78 mmoles), diisopropylethylamine (0.9 mL), acetic anhydride (1.9 mL) in dimethylformamide (5 mL) for 1 hour at room temperature on a shaker. The resin was then washed three times with dimethylformamide (7 mL each time), twice with diethyl ether (7 mL each time), and four times with CHCl$_3$ (7 mL each time). The peptide was de-protected and cleaved from the resin using TFA (9 mL) in the presence of triisopropysilane (400 μL, 2 mmoles) and 1,2-ethanedithiol (0.2 mL, 6.4 mmoles) for 2.5 hours at room temperature on a shaker. The solution was drained into 1% acetic acid/water (180 mL), and washed three times with CHCl$_3$ (80 mL each time) and three times with diethyl ether (80 mL each time). The aqueous layer was then concentrated to a solid and lyophilized from 0.1% TFA in water. The crude peptide was purified using a 9% acetonitrile/water (0.1% TFA) isocratic mixture on a C-18 reversed phase HPLC column (3 mL/min, retention time 10-12 min) and lyophilized to yield a white solid (40 mg, 10%). MALDI TOF MS calculated for C$_{59}$H$_{118}$N$_{38}$O$_{115}$: 1566.96. found 1567.82 [M+H]$^+$.

Using the purified peptide ace-CRRRRRRRR-am trifluoroacetic acid made as described above, the final product BODIPY-Cys(Arg)$_9$ hydrochloride shown as (5) on Scheme X, was then prepared. The purified peptide ace-CRRRRRRRR-arm trifluoroacetic acid (10 mg, 3.86 umoles) was dissolved in an aqueous degassed buffer (1 mL of 100 mM NaCl, 10 mM phosphate pH 7.5, Ar sparged) and treated (dropwise) with a solution of BODIPY Cl-IA (1.3 mg, 3-1 μmoles, 0.81 equivalent, Molecular Probes) that was pre-dissolved in DMSO (1.25 mL). The reaction was allowed to react in the dark for 1 h at room temperature, the product was then diluted with 8 mL of water and loaded onto an activated C-18 reversed-phase cartridge (Waters, Sep-pack). The column was washed with 5% acetonitrile (5 mL containing 100 mM of NaCl in water) and 1 mL pure water. The product eluted between 0-20% acetonitrile (in water) and was lyophilized to yield 3.8 mg (56% yield) of a red powder. All BODIPY-glycoside conjugates are slightly to moderately hygroscopic, therefore the absorption at 502 nm (in methanol) of each compound was used to confirm the yield of the conjugation reaction (taking ε502 nm=76,000 cm$^{-1}$ M$^{-1}$).

$^1$H-NMR (400 MHz, D$_2$O) δ 7.43 (s, 1H), δ 6.91 (d, J=3.6 Hz, 1H), δ 6.29 (d, J=3.6 Hz, 1H), δ 6.25 (s, 1H), δ 4.53 (s, 2H), δ 4.32 (t, J=7.2 Hz, 1H), δ 4.13-4.23 (m, 10H), δ 3.34 (s, 2H), δ 2.96-3.08 (m, 18H), δ 2.86 (d, J=6.8 Hz, 2H), δ 2.42 (s, 3H), δ 2.17 (s, 3H), δ 1.89 (s, 3H), δ 1.50-1.71 (m, 36H). The $^1$H NMR suggests better than 95% purity for this, and all other compounds evaluated. MALDI TOF MS calculated for C$_{73}$H$_{132}$BF$_2$N$_{41}$O$_{12}$S: 1856. found 1857 [M+H]$^+$.

Example 6

Synthesis and Characterization of tris-BODIPY

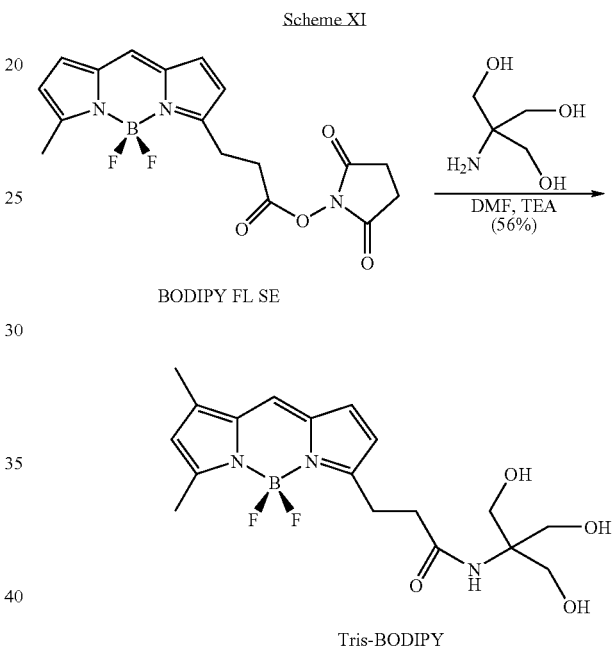

A scheme for synthesizing tris-BODIPY is shown below (Scheme XI):

To synthesize tris-BODIPY, the following procedure was used. BODIPY FL SE (Molecular Probes) (~0.4 mg, ~1 μmoles) was dissolved in dimethylformamide (1 ml), and treated with Trisma base (10 mg, 126 μmoles) and triethylamine (10 μl, 72 μmoles) for 1 hour at room temperature in the dark. The product was diluted with 8 ml of 50 mM phosphate (pH=7.5) and loaded onto an activated C-18 reversed-phase cartridge (Waters, Sep-pack). The column was washed with 5 ml of pure water. The desired product eluted with 30% acetonitrile (in water), and was lyophilized to yield ~0.2 mg (56% yield) of a red powder. All BODIPY-glycoside conjugates are slightly to moderately hygroscopic, therefore the absorbance at 502 nm (in methanol) of each compound is used to calculate the yield of the conjugation reaction (taking ε502 nm=76,000 cm$^{-1}$ M$^{-1}$). $^1$H-NMR (400 MHz, MeOD) δ 7.43 (s, 1H), δ 7.00 (d, J=4.0 Hz, 1H), δ 6.35 (d, J=4.0 Hz, 1H), δ 6.21 (s, 1H), δ 3.71 (s, 6H), δ 3.21 (t, J=8.0 Hz, 2H), δ 2.68 (t, J=8.0 Hz, 2H), δ 2.50 (s, 3H), δ 2.28 (s, 3H), ESI MS calculated for C$_{18}$H$_{24}$BF$_2$N$_3$O$_4$: 395.2. found 418.3 [M+Na]$^+$

Example 7

Synthesis and Characterization of Amino-Tobra-Fluorescein

A scheme for synthesizing amino-tobra-fluorescein is shown below (Scheme XII):

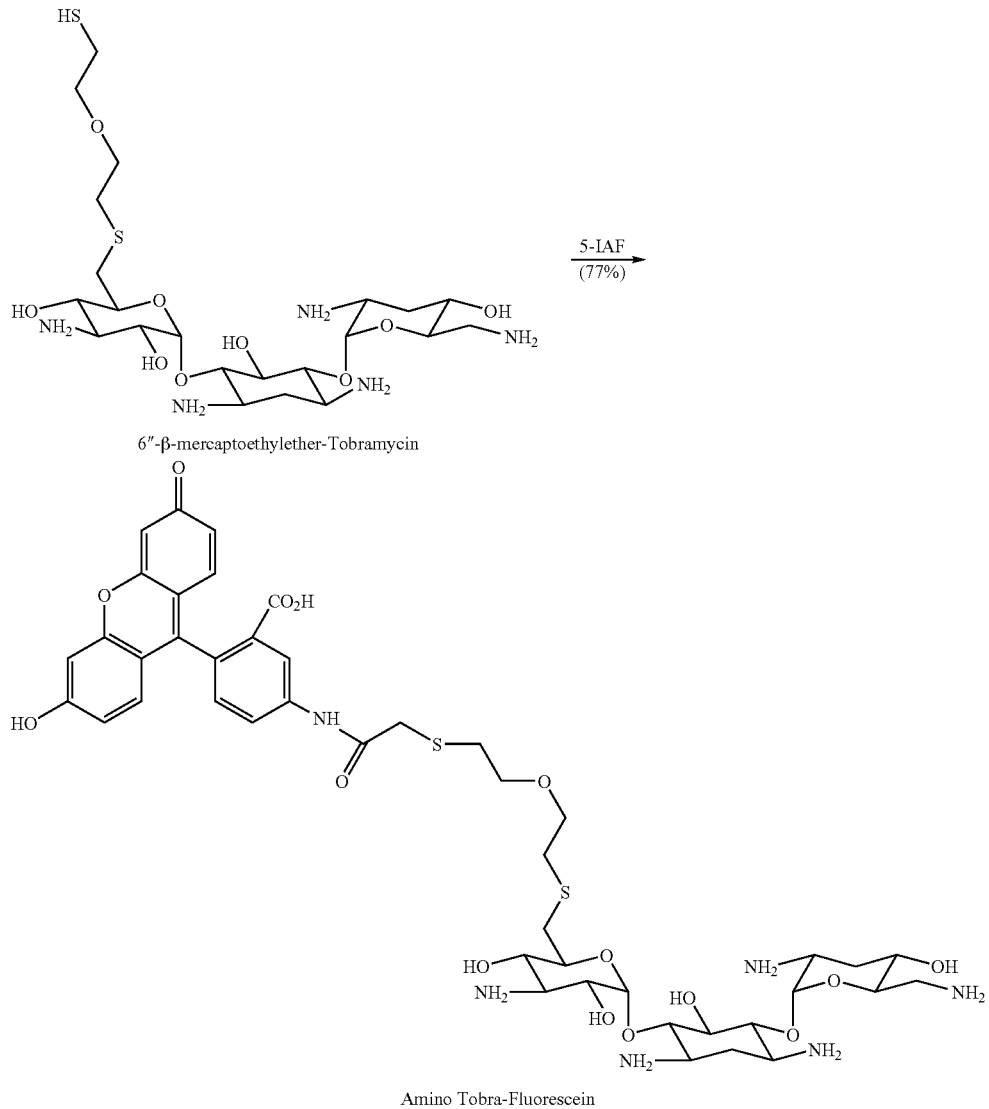

6"-β-mercaptoethyl ether tobramycin trifluoroacetic acid, prepared as described in Example 1 (3 mg, 2.6 µmoles), was dissolved in an aqueous degassed buffer, (2 mL of 400 mM NaCl, 25 mM sodium phosphate, pH=7.5, Ar sparged), separately 5-iodo-acetamido-fluorescein (5-IAF) (3.0 mg, 5.8 µmoles, 2.0 equivalent, Molecular Probes) was dissolved in dimethylsulforide (1 mL), and added, dropwise, to the tobramycin solution and allowed to react in the dark for 2 h at room temperature, followed by adding 0.1M HCl, until the solution turned from orange to yellow. The product was then diluted with water (8 mL) and loaded onto an activated C-18 reversed-phase cartridge (Waters, Sep-pack), the column was then washed with pure water (10 mL), and the product was eluted with 20% acetonitrile/water, lyophilized, and found to be >95% pure by HLPC. The product was purified further using a C-18 reversed phase HPLC column with an isocratic mixture of 20% acetonitrile (0.1% TFA) in water (0.1% TFA) (3 mL/min) ($R_f$=8.5 min) to yield 3.3 mg (77%) of an orange solid. All fluorescein-glycoside conjugates are slightly to moderately hygroscopic, therefore the absorption at 496 nm (in aqueous buffer pH 9.0) of each compound is used to confirm the yield of the conjugation reaction (taking $\epsilon_{502\ nm}$=77,000 cm$^{-1}$ M$^{-1}$). $^1$H-NMR (400 MHz, D$_2$O) δ 8.13 (d, J=2.0 Hz, 1H), δ 7.67 (d, d J$_1$=8.4 Hz, J$_2$=1.6 Hz, 1H), δ 7.15-7.22 (m, 3H), δ 6.93 (d, J=2.4 Hz, 2H), 6.77-6.80 (m, 2H), δ 5.53 (d, J=2.8 Hz, 1H), δ 4.85 (d, J=3.6 Hz, 1H), δ 3.22-3.83 (m, 21H), δ 3.05 (d, d J$_1$=13.2 Hz, J$_2$=7.2 Hz, 1H), δ 2.87 (d, d J$_1$=11.6 Hz, J$_2$=2.0 Hz, 1H), δ 2.77 (t, J=5.8 Hz, 2H), δ 2.57-2.65 (m, 3H), δ 2.36 (d, t J$_1$=12.0 Hz, J$_2$=3.6 Hz, 1H), δ 2.09 (d, t J$_1$=12.4 Hz, J$_2$=3.6 Hz, 1H), δ 1.83 (q, J=11.6 Hz, 1H), δ 1.74 (q, J=12.4 Hz, 1H). MALDI TOF MS calculated for C$_{44}$H$_{58}$N$_6$O$_{15}$S$_2$: 974.34. found 975.42 [M+H]$^+$. found 997.43 [M+Na]$^+$. found 1013.41 [M+K]$^+$.

Example 8

Synthesis and Characterization of Guanidino Tobra-Fluorescein

A scheme for synthesizing guanidino-tobra-fluorescein is shown below (Scheme XIII):

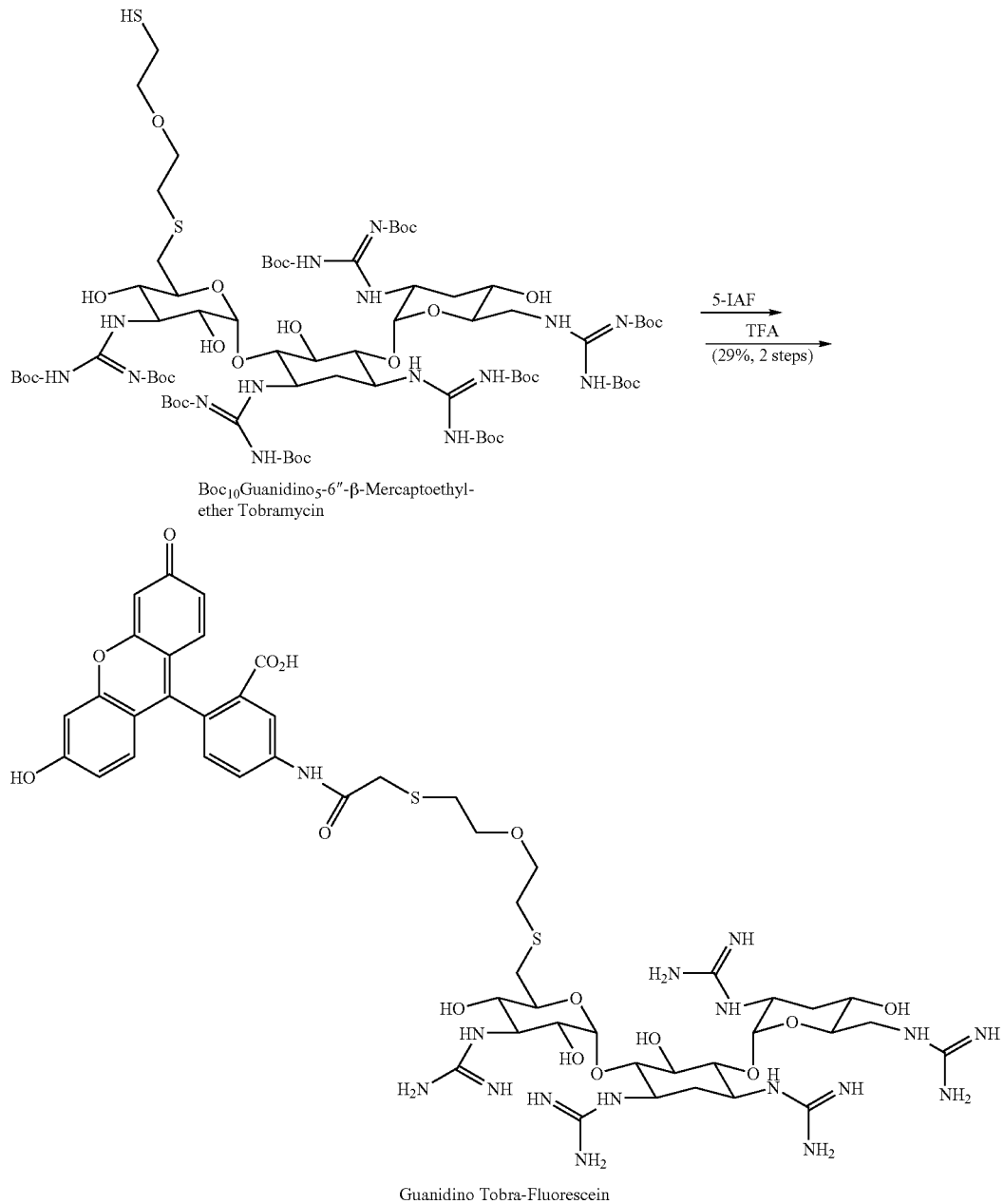

Boc$_{10}$-guanidino$_5$-6"-β-mercaptoethylether tobramycin synthesized as described in Example 2 (10 mg, 5.6 μmoles), dimethylformamide (3 mL), Cs$_2$CO$_3$ (30 mg), and 5-iodo-acetamido-fluorescein (5-IAF) (5 mg, 9.7 μmotes, 1.7 equivalent, Molecular Probes) were stirred at room temperature in the dark for 2 hours, then diluted with ethyl acetate (150 mL) and twice washed with 1M Na$_2$CO$_3$ (50 mL each time), twice with 0.1M citric acid (50 mL each time), brine (50 mL), dried over sodium sulfate then concentrated under reduced pressure to a solid. The product was then de-protected using triisopropyl silane (0.15 mL) and trifluoroacetic acid (3 mL), in CHCl$_3$ (1 mL) for 2.5 hours at room temperature. Excess anhydrous toluene was then added and all volatile products were removed at 50° C. under reduced pressure. The product was then diluted with water (8 mL) and loaded onto an activated C-18 reversed-phase cartridge (Waters, Sep-pack), the column was then washed with pure water (10 mL), and the product eluted at 20% acetonitrile/water, lyophilized, and found to be >95% pure (by HLPC). The final product was purified further using a C-18 reversed phase HPLC column with an isocratic mixture of 20% acetonitrile (0.1% trifluoroacetic acid) in water (0.1% trifluoroacetic) (3 mL/min) (R$_t$=11.5 min) to yield 2.3 mg (29%, 2 steps) of an orange solid. All fluorescein-glycoside conjugates are slightly to moderately hygroscopic, therefore the absorption at 496 nm (in aqueous buffer having pH=9.0) was used to confirm the yield of the conjugation reaction (taking $\epsilon_{502\,nm}$=77,000 cm$^{-1}$ M$^{-1}$). $^1$H-NMR (400 MHz, D$_2$O) δ 8.17 (d, J=2.0 Hz, 1H), δ 7.70 (d, d J$_1$=10 Hz, J$_2$=1.6 Hz, 1H), δ 7.15-7.20 (m, 3H), δ 6.97 (d, J=1.6 Hz, 2H), 6.79-6.80 (m, 2H), δ 5.19 (d, J=3.2 Hz, 1H), δ 4.91 (d, J=2.8 Hz, 1H), δ 3.95 (t, J=6.8 Hz, 1H), δ 3.20-3.60 (m, 23H), δ 2.80 (d, d J$_1$=11.2 Hz, J$_2$=2.4 Hz, 1H), δ 2.77 (t, J=5.8 Hz, 2H), δ 2.51-2.60 (m, 4H), δ 1.97-2.07 (m, 2H), δ 1.48-1.53 (m, 2H). MALDI TOF MS calculated for $C_{49}H_{68}N_{16}O_{15}S_2$: 1184.45. found 1185.63 [M+H]$^+$. found 1207.60 [M+Na]$^+$.

Example 9

Synthesis and Characterization of Guanidino-Neo-Fluorescein

A scheme for synthesizing guanidino-neo-fluorescein is shown below

Boc$_{12}$-guanidino$_6$-5″-β-mercaptoethylether neomycin B prepared as described in Example 4 (3 mg, 1.4 μmoles), dimethylformamide (0.5 mL), 5-iodo-acetamido-fluorescein (5-IAF) (5 mg, 9.7 μmoles, 1.7 equivalent, Molecular Probes), and triethyl amine (20 μL) were stirred at room temperature in the dark for 2 hours, then diluted with ethyl acetate (150 mL) and washed four times with 1M Na$_2$CO$_3$ (50 mL each time), twice with 0.1M citric acid (50 mL each time), and brine (50 mL), dried over sodium sulfate then concentrated under reduced pressure to a solid. All of this product was then de-protected using triisopropyl silane (0.05 mL) and trifluoroacetic acid (5 mL), in CHCl$_3$ (3 mL) for 3.5 hours at room temperature. Excess anhydrous toluene was then added and all volatile products were removed at 50° C. under reduced pressure. The product was then diluted with water (8 mL, 300 mM NaCl) and loaded onto an activated C-18 reversed-phase cartridge (Waters, Sep-pack), the column was then washed with pure water (10 mL), and the product eluted between 5-20% acetonitrile/water (0.001 M HCl), lyo-

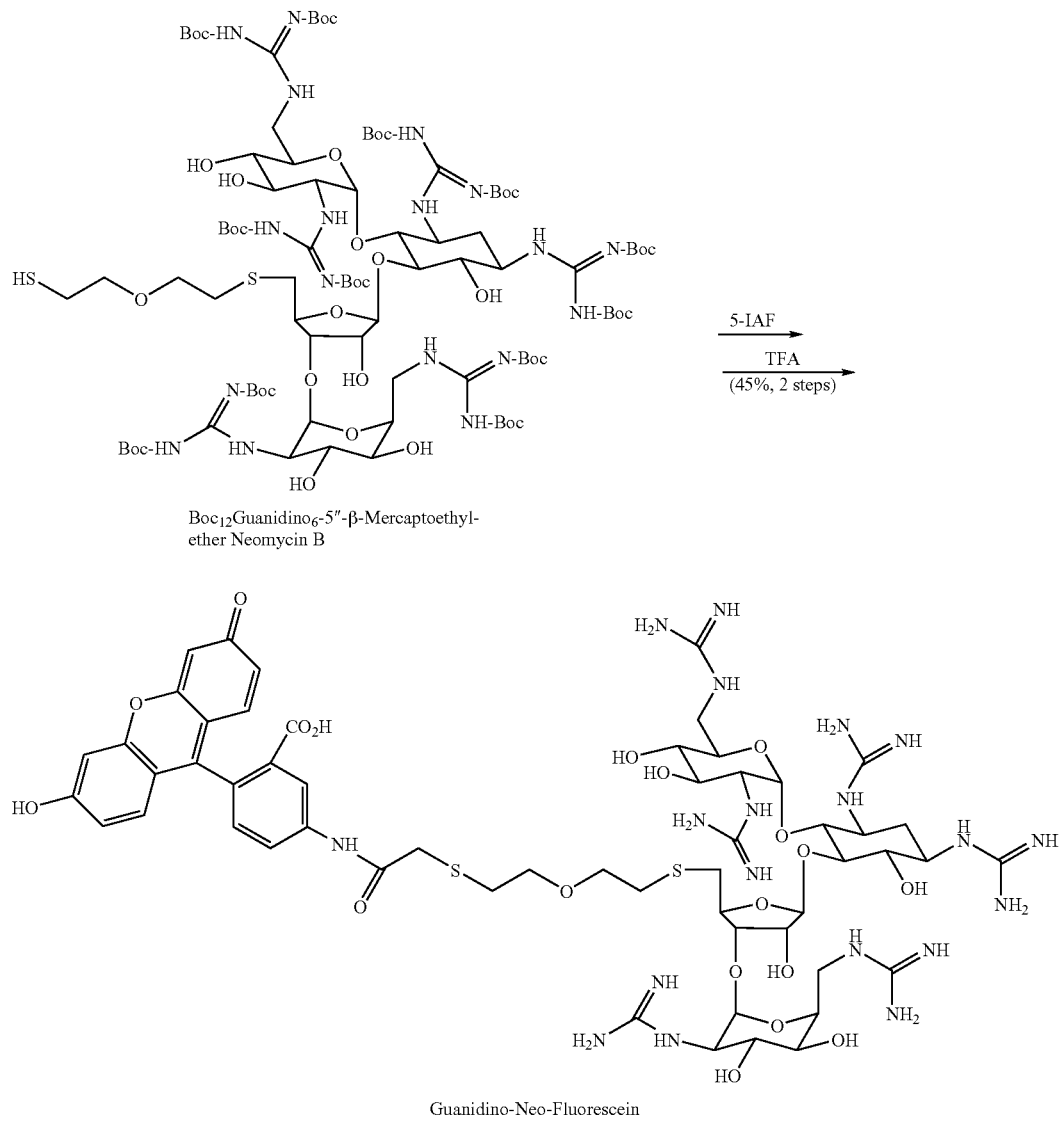

Scheme XIV philized, and found to be >85% pure (by HLPC). The product was purified further using a C-18 reversed phase HPLC column with an isocratic mixture of 20% acetonitrile (0.1% trifluoroacetic acid) in water (0.1% trifluoroacetic acid) (3 mL/min) ($R_t$=9.3 min) to yield 1.3 mg (45%, 2 steps) of an orange solid. All fluorescein-glycoside conjugates are slightly to moderately hygroscopic, therefore the absorption at 496 nm (in aqueous buffer pH 9.0) was used to confirm the yield of the conjugation reaction (taking $\epsilon_{502\,nm}$=77,000 $cm^{-1}$ $M^{-1}$). $^1$H-NMR (400 MHz, $D_2O$): δ 8.12 (d, J=2.0 Hz, 1H), δ 7.72 (d, d $J_1$=8.8 Hz, $J_2$=1.6 Hz, 1H), δ 7.22 (d, J=8.8 Hz, 1H), δ 7.11 (d, J=9.2 Hz, 2H), δ 6.92 (d, J=2.4 Hz, 2H), δ 6.76 (d, d $J_1$=8.8 Hz, $J_2$=2.4 Hz, 1H), δ 5.69 (d, J=4.0 Hz, 1H), δ 4.98 (s, 1H), δ 4.87 (s, 1H), δ 4.18-4.24 (m, 2H), δ 3.85-3.88 (m, 3H), δ 3.16-3.62 (m, 18H), δ 2.71-2.78 (m, 4H), δ 2.42-2.52 (m, 4H), δ 2.01 (d t, $J_1$=12.0 Hz, $J_2$=4.4 Hz, 1H), δ 1.48 (q, J=12.0 Hz, 1H). MALDI TOF MS calculated for $C_{55}H_{79}N_{19}O_{19}S_2$: 1373.53. found 1374.72 $[M+H]^+$.

Example 10

Study of Cellular Uptake

10T½ cells, an adherent non-transformed mouse fibroblast cell line, were purchased from ATCC and used before their 20th passage. HeLa cells, a common human cancer cell line, were a gift from Dr. Susan S. Taylor. Both cell lines were cultured in Dulbecco's modified eagle medium containing 10% fetal bovine serum at 37° C. in an 8% $CO_2$ environment. For each experiment, cells were seeded onto 4 cm tissue culture plates (Nunc) and allowed to grow overnight to ~80% confluency.

Compounds 1-5 identified in Table 1, below (0.5-1 μM), were added to each dish and incubated at 37° C./8% $CO_2$ for 0.5-1 hr. Cells were then washed once in PBS, trypsinized with 500 μl ATV solution (Gibco) for 3 minutes, pelleted in a fixed angle centrifuge for 5 minutes at 5,000×G, then brought up in 1 mL PBS. Each sample was quickly (within 5 minutes) analyzed on a FACS VantageSE cell sorter (Becton-Dickinson) using the 488 nm argon/krypton laser line and a 530 nm band pass emission filter. 2,000-10,000 cells were counted per sample.

The uptake of BODIPY-containing glycosides by two different eukaryotic cell lines was also studied using fluorescence microscopy.

TABLE 1

Summary of the Mean Fluorescence Intensities of Treated Cells According to FACS[a]

| Compound | 10T1/2[b] | HeLa[c] |
| --- | --- | --- |
| None (auto-fluorescence) | ~40[d] | 830 |
| Tobra-BODIPY (1) | 60 | 1,000 |
| Guanidino-Tobra-BODIPY (2) | 240 | 2,100 |
| Neo-BODIPY (3) | 60 | ~1,400[e] |
| Guanidino-Neo-BODIPY (4) | 430 | 7,900 |
| BODIPY-Cys (Arg)$_9$ (5) | 280 | 2,000 |
| BODIPY-Cys(arg)$_9$ (5) + 10 μM (6) | 110 | n.d.[f] |
| BODIPY-Cys(arg)$_9$ (5) + 50 μM (6) | 90 | n.d. |
| BODIPY-Cys(arg)$_9$ (5) + 200 μM (6) | 70 | n.d. |

[a]The data between cell types are not directly comparable, as a higher instrumental gain (about 10-fold) was used for the HeLa experiments.
[b]Average intensity of 10,000 individual cells treated with 0.5 μM of each compound for 1 hr.
[c]Average intensity of 2,000 individual cells treated with 1 μM of each compound for 0.5 hr. Under these conditions a "free" BODIPY dye molecule Tris-BODIPY shows poor uptake into HeLa cells (similar to Tobra-BODIPY).
[d]Estimate based upon data set collected at a higher instrument gain,
[e]Estimate based upon data set collected at a lower instrument gain.
[f]n.d. = not determined.

Figure 3:
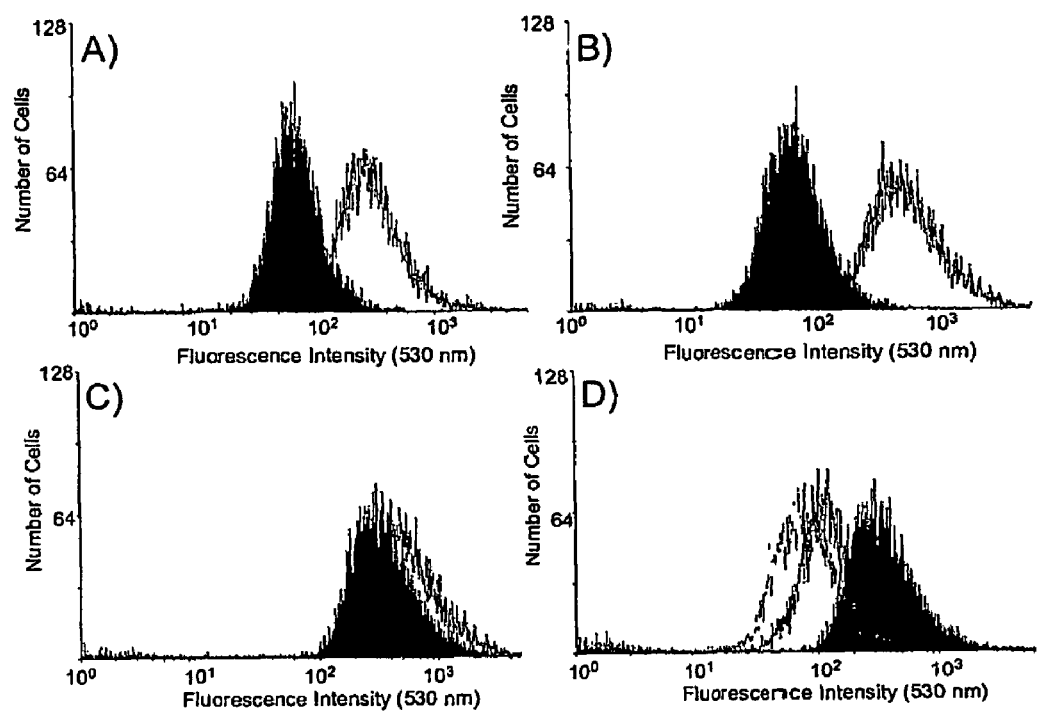
FIG. 3 presents FACS histograms showing the fluorescence intensity versus cell count.

Examples of FACS histograms are presented in FIG. 3, which illustrates the fluorescence intensity versus cell count for 10,000 individual 10T½ cells following a 1 hour incubation with 0.5 μM of: (A) tobra-BODIPY (Red) and guanidine-tobra-BODIPY (White); (B) neo-BODIPY (Red) and guanidine-neo-BODIPY (White); (C) BODIPY-Cys(Arg)$_9$ (Red), or guanidine-neo-BODIPY (White); and (D) uptake of BODIPY-Cys(Arg)$_9$ inhibited by guanidine-neomycin B (6) at 0 μM (Red), 10 μM (Black), 200 μM (Green).

Some microscopy images are shown in FIGS. 4, 6, 7 and 8. In a typical experiment, cell cultures were treated with 0.5-5 μM of each compound for 0.5-1 hr, washed twice with buffer, cleaved with trypsin, and quantified for fluorescence at 530 nm.

Figure 4:
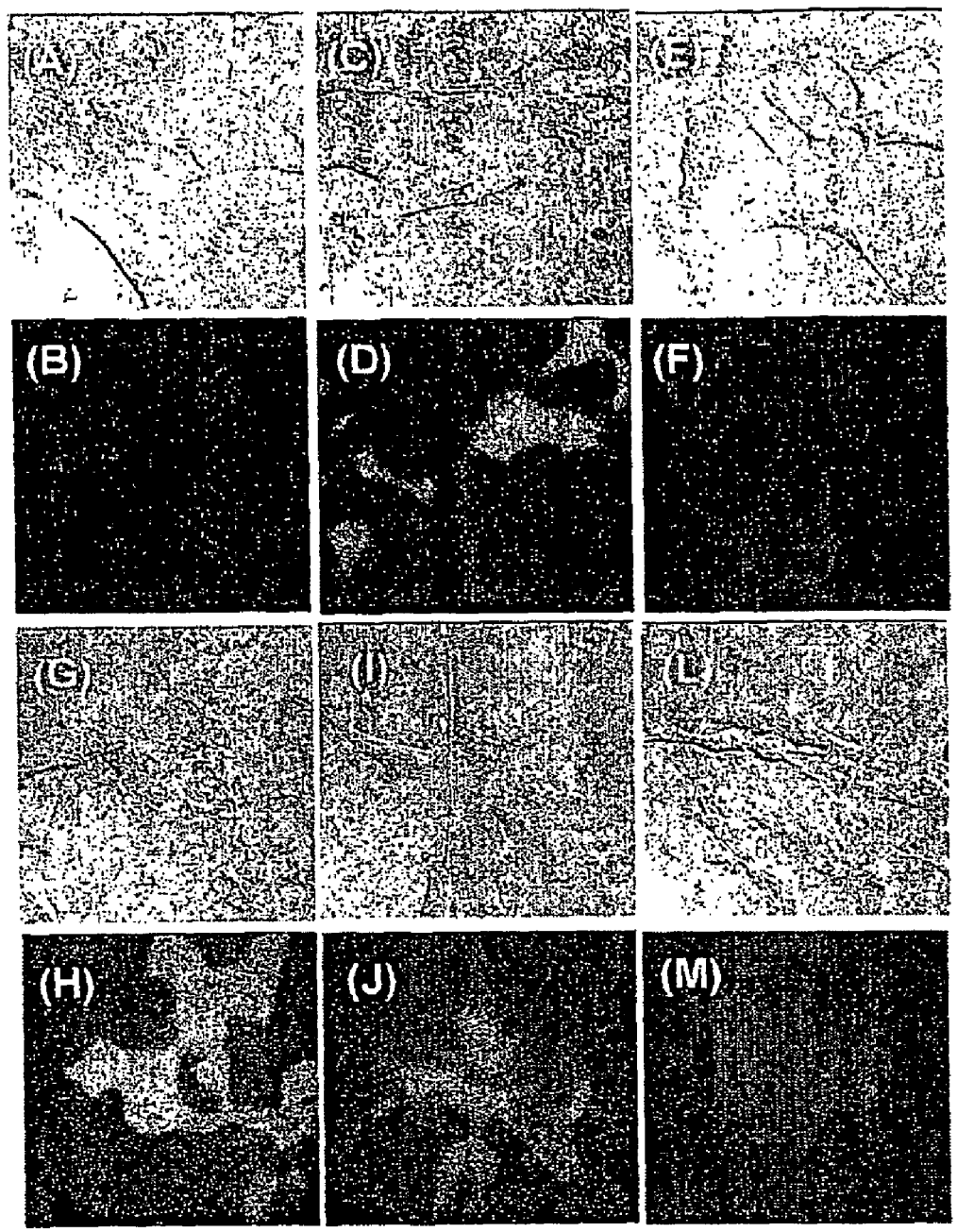
FIG. 4 illustrates cellular uptake of the fluorescein-labeled aminoglycosides and guanidinoglycosides into 10T½ cells that are adhered to culture plates.
Figure 5:
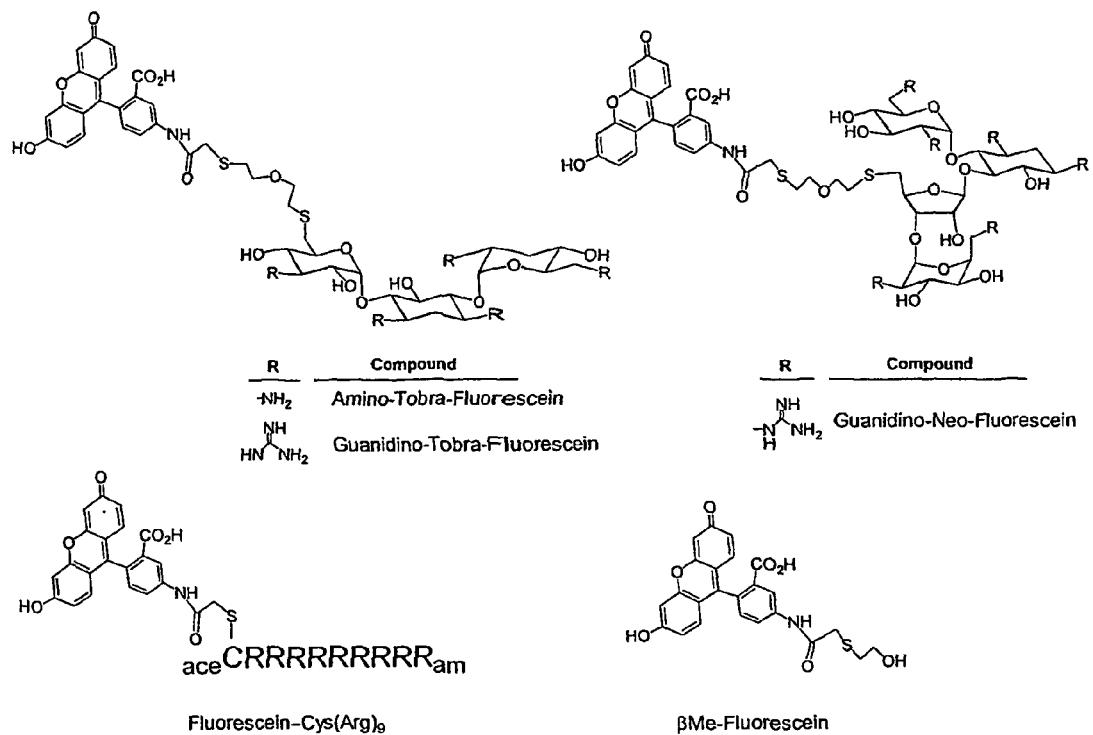
FIG. 5 illustrates structures of fluorescein-containing compounds.

FIG. 4 illustrates cellular uptake of the fluorescein-labeled aminoglycosides and guanidinoglycosides into 10T½ cells that are adhered to culture plates. For each sample, both fluorescence emission (B, D, F, H, J, M) and white light differential interference contrast (A, C, E, G, I, L) are shown. Each sample is treated with 1 μM of each compound for 1 hr, washed two times with buffer and imaged as described above. Shown are: amino tobra-mycinfluorescein (A and B), guanidine-tobra-fluorescein (C and D), amino-neo-BODIPY (E and F), guanidine-neo-fluorescein (G and H), fluorescein-$CR_9$ (I and J) and the control dye "βMe-fluorescein" (L and M).

Figure 6:
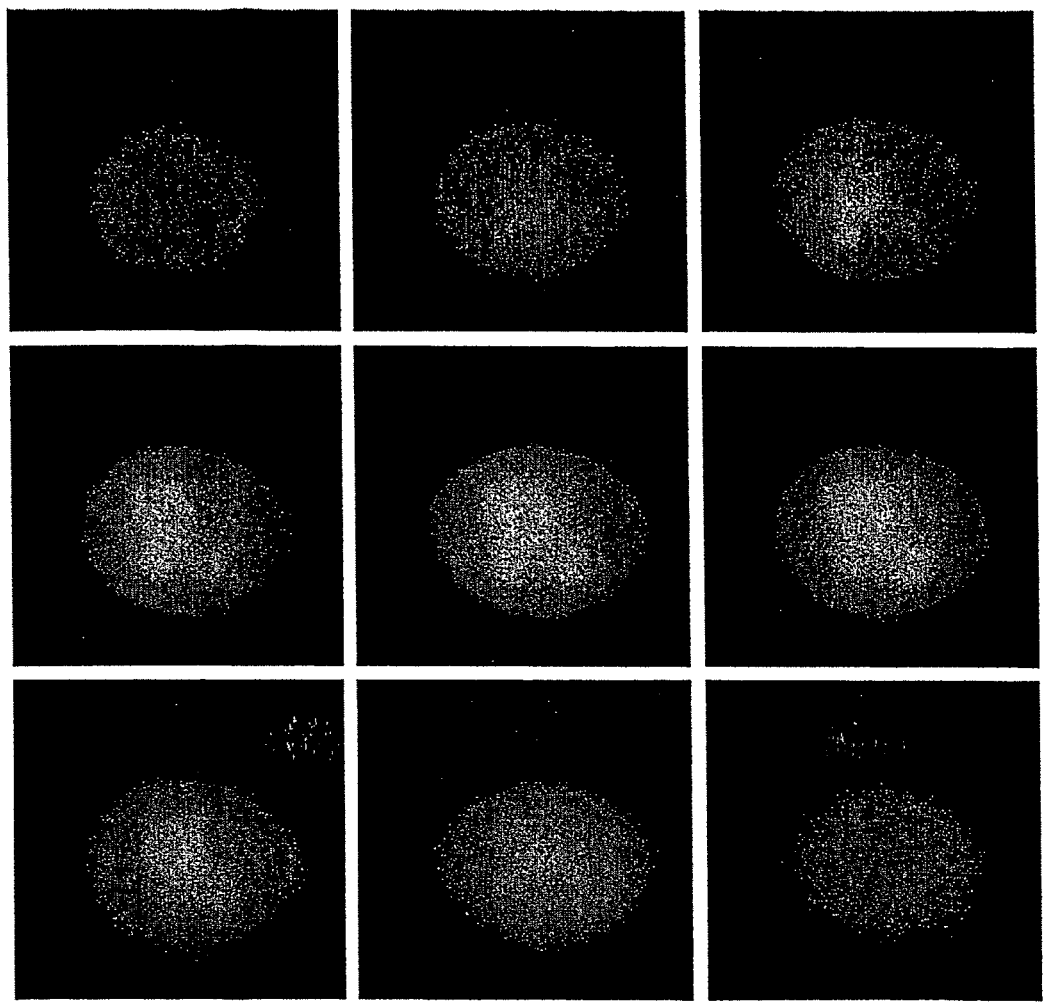
FIG. 6 shows an example of distribution type 1 (diffuse cytoplasmic, nuclear and nucleolar localization).

FIG. 6 shows an example of distribution type 1 (diffuse cytoplasmic, nuclear and nucleolar localization). 0.5 μm cross-sectional images of a single HeLa cell in solution are shown.

Figure 7:
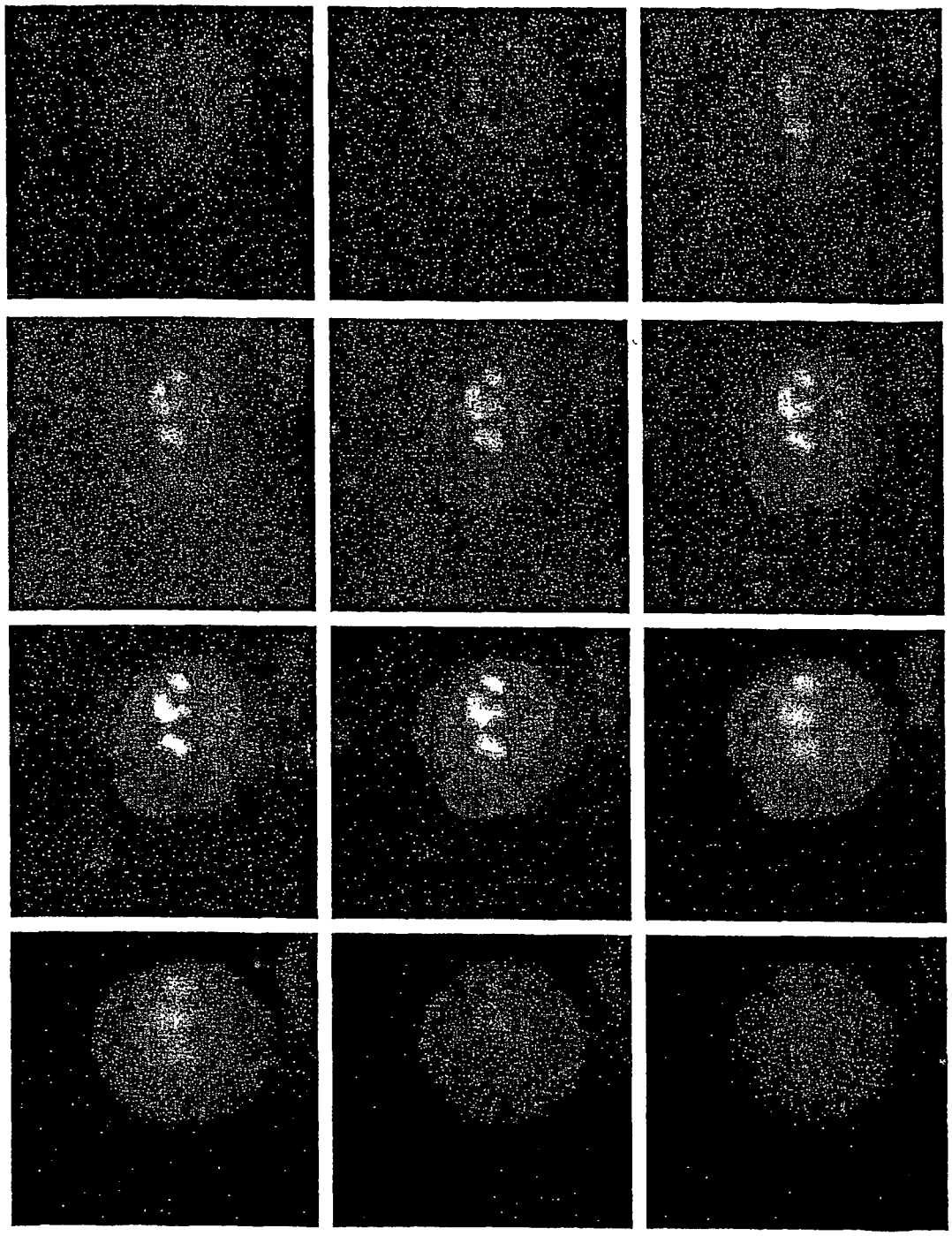
FIG. 7 shows an example of distribution type 2 (mainly nuclear and nucleolar localization).

FIG. 7 shows an example of distribution type 2 (mainly nuclear and nucleolar localization). 0.5 μm cross-sectional images of a single HeLa cell in solution are shown.

Figure 8:
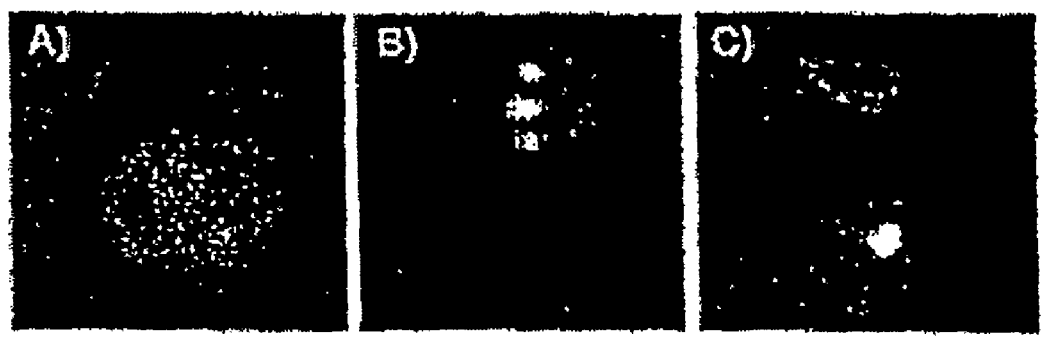
FIG. 8 shows microscopy experiments for fluorescein- and BODIPY-labeled guanidinoglycosides.

FIG. 8 shows microscopy experiments for fluorescein- and BODIPY-labeled guanidinoglycosides. (A) and (B) show cross-sectional images of two individual HeLa cells in solution following a 30 minute treatment with 5 μM of guanidine-neo-BODIPY and cleavage with trypsin. (C) shows two neighboring 10T½ cells growing on a culture plate following a 1 hr exposure to 1 μM of 4.

As can be seen, both fluorescent aminoglycosides (1 and 3, see FIG. 3) display poor cellular uptakes (slightly above the autofluorescence of the cell itself) (Table 1).

Upon guanidinylation, the cellular uptake of tobramycin is enhanced by approximately 10-fold (relative to autofluorescence), and the enhancement for neomycin B is approximately 20-fold (see, FIGS. 3, (A) and (B) and Table 1). The type of molecular scaffold used for the display of guanidinium groups has a profound impact on the efficiency of uptake.

Compared to a common poly-Arg transduction peptide, the guanidinoglycosides show the same, or even better cellular uptake efficiencies. Guanidino-tobra-BODIPY (2 in Table 1) has 4 fewer guanidinium groups as BODIPY-Cys(Arg) (5 in Table 1), but shows approximately the same transport efficiency. Importantly, guanidine-neo-BODIPY (4 in Table 1) consistently has a better cellular uptake as compared to the poly-Arg peptide BODIPY-Cys(Arg) (5 in Table 1) (FIG. 3 (C), Table 1). This suggests that the semi-rigid pre-organization of the guanidinium groups on the glycoside core may better facilitate translocation across the cell membrane. In contrast to the results obtained for a family of poly-Arg peptoids, the flexible amphipathic properties usually provided by the methylene chains of poly(Arg) residues do not appear essential for membrane transport of guanidinoglycosides. To address the possibility that guanidine-neomycin B enters cells through a different mechanism than poly-Arg, a competition experiment was conducted between BODIPY-Cys (Arg) (5 in Table 1 and the unlabeled guanidine-neomycin B (6, see FIG. 2). FACS analysis shows that guanidine-neomycin B (6, see FIG. 2) effectively inhibits the transport of BODIPY-Cys(Arg) into cells (FIG. 3 (D) and Table 1), suggesting a common pathway responsible for the uptake of both compounds.

Microscopy experiments have been conducted using both fluorescein-labeled and BODIPY-labeled guanidinoglycosides. The relative intensities of individual cells, following treatment with either fluorescent aminoglycosides or guanidinoglycosides are consistent with the trends from FACS experiments. Optical cross sectioning using scanning confocal fluorescence microscopy indicates that guanidinoglycosides are found inside of living cells (FIG. 8). Interestingly, two distinct types of cellular localization of guanidino-neo-BODIPY are observed (FIG. 8). Approximately half of the cells exhibit a highly diffuse, cytoplasmic and nuclear distribution (FIG. 6), while the other half exhibit more localized nucleolar staining, similar to that reported for poly-Arg peptides (FIG. 7). Similar results were observed with fluorescein-labeled conjugates, as well as 10T½ cells (FIG. 8). Taken together, this suggests that the relative uptake efficiencies and cellular localization of these compounds are not highly dependent on cell type or dye molecules used.

In summary, unlike aminoglycosides, guanidinoglycosides exhibit highly efficient uptake by eukaryotic cell cultures via a similar mechanism as a poly-arginine peptide.

Example 11

Evaluation of HIV-1 Inhibitory Activity

The analytically pure and fully characterized conjugates will be tested for their ability to inhibit HIV replication in HIV-1 infected CD44 HeLa cells by following their inhibition of plaque formation. The decrease in viral load in infected human peripheral blood monocytes (determined by standard p24 ELISA) will also be carried.

The performance of the AZT-guanidino-neomycin B conjugate, for example, can be evaluated against the individual components. These controls include: 1) AZT alone, 2) linker alone, 3) guanidino-neomycin B alone, 4) AZT+guanidino-neomycin B, 5) AZT-monophosphate alone, and 6) AZT-monophosphate+guanidine-neomycin B. In each case dose-dependent curves will be generated in triplicates.

Although the invention has been described with reference to the above examples, it will be understood that modifications and variations are encompassed within the spirit and scope of the invention. Accordingly, the invention is limited only by the following claims.

What is claimed is:

1. A composition comprising a therapeutically active compound covalently bonded to a guanidinoaminoglycoside; wherein the therapeutically active compound is selected from the group consisting of a nucleic acid, nucleoside, protein, peptide, amino acid residue, and dye.

2. The composition of claim 1, wherein the therapeutically active compound is selected from the group consisting of a nucleoside, amino acid residue and dye.

3. The composition of claim 1, wherein the therapeutically active compound comprises a nucleoside, wherein the nucleoside is a reverse transcriptase inhibitor.

4. The composition of claim 3, wherein the reverse transcriptase inhibitor is selected from the group consisting of 3'-azido-3'-deoxythymidine, 2',3'-dideoxyinosine and 2',3'-dideoxycytidine.

5. The composition of claim 1, wherein the guanidinoaminoglycoside is selected from the group consisting of guanidino-amikacin, guanidino-gentamicin, guanidino-kanamycin, guanidino-neomycin, guanidino-netilmicin, guanidino-O-2,6-diamino-2,6-dideoxy-beta-L-idopyranosyl-(1 to 3)-O-beta-D-ribofuranosyl-(1 to 5)-O-[2-amino-2-deoxy-alpha-D-glucopyranosyl-(1 to 4)]-2-deoxystreptamine, guanidino-streptomycin and guanidino-tobramycin.

6. A method of increasing the cellular uptake of a therapeutically active compound, comprising:
(a) modifying a dialkoxy substance, wherein the dialkoxy substance is an aminoglycoside, by treating the dialkoxy substance with a guanidinylating reagent to form an adduct, wherein the adduct is a guanidinoaminoglycoside;
(b) covalently bonding the adduct to the therapeutically active compound to form a conjugate, wherein the therapeutically active compound is selected from the group consisting of a nucleic acid, nucleoside, protein, peptide, amino acid residue, and dye; and
(c) delivering the conjugate to a cell.

7. The method of claim 6, wherein the aminoglycoside comprises a cyclic acetal.

8. The method of claim 6, wherein the guanidinylating reagent comprises a guanidine or alkylguanidine moiety.

9. The method of claim 6, wherein the aminoglycoside comprises at least one cyclic acetal having the formula:

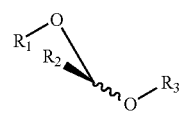

wherein $R_1$, $R_2$, and/or $R_3$ groups comprise two or more 5- or 6-membered rings which are linked together by at least one acetal functional group and wherein $R_1$-$R_2$, and $R_3$ are the carbon atoms of two separate ring systems.

10. The method of claim 9, wherein in treating the aminoglycoside, the guanidinylating reagent is reacted with at least one primary or secondary alcohol of the aminoglycoside to produce a guanidinoaminoglycoside.

11. The method of claim 10, wherein the guanidinylating reagent has the general formula:

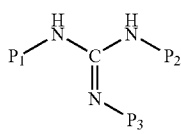

wherein each of $P_1$, $P_2$ and $P_3$ is, independently, the same or different protecting group, each protecting group having the general structure:

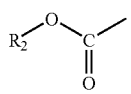

wherein $R_2$ is a substituted or unsubstituted alkyl, aryl, or heterocyclic group.

12. The method of claim 9, wherein in treating the aminoglycoside, the guanidinylating reagent is reacted with at least one primary or secondary amine of the aminoglycoside to produce a guanidinoaminoglycoside.

13. The method of claim 12, wherein the guanidinylating reagent has the general formula:

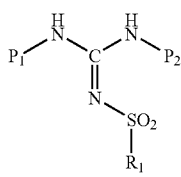

wherein $R_1$ is trifluoromethyl group, and each of $P_1$, $P_2$ and $P_3$ is, independently, the same or different protecting group, each protecting group having the general structure:

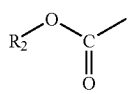

wherein $R_2$ is a substituted or unsubstituted alkyl, aryl, or heterocyclic group.

14. The method of claim 6, wherein the aminoglycoside is selected from the group consisting of amikacin, gentamicin, kanamycin, neomycin, netilmicin, O-2,6-diamino-2,6-dideoxy-beta-L-idopyranosyl-(1 to 3)-O-beta-D-ribofuranosyl-(1 to 5)-O-[2-amino-2-deoxy-alpha-D-glucopyranosyl-(1 to 4)]-2-deoxystreptamine, streptomycin, and tobramycin.

15. The method of claim 6, wherein the therapeutically active compound is selected from the group consisting of a nucleoside, amino acid residue and dye.

16. The method of claim 6, wherein the therapeutically active compound comprises a nucleoside, wherein the nucleoside is a reverse transcriptase inhibitor.

17. The method of claim 16, wherein the reverse transcriptase inhibitor is selected from the group consisting of 3'-azido-3'-deoxythymidine, 2',3'-dideoxyinosine and dideoxycytidine.

18. The method of claim 16, wherein the guanidinoaminoglycoside is selected from the group consisting of guanidino-amikacin, guanidino-gentamicin, guanidino-kanamycin, guanidino-neomycin, guanidino-netilmicin, guanidino-O-2,6-diamino-2,6-dideoxy-beta-L-idopyranosyl-(1 to 3)-O-beta-D-ribofuranosyl-(1 to 5)-O-[2-amino-2-deoxy-alpha-D-glucopyranosyl-(1 to 4)]-2-deoxystreptamine, guanidino-streptomycin and guanidino-tobramycin.

19. The method of claim 9, wherein in treating the aminoglycoside, the guanidinylating reagent is reacted with at least one primary or secondary alcohol of the aminoglycoside to produce a guanidinoaminoglycoside.

20. The composition of claim 1, wherein the therapeutically active compound in the conjugate is covalently bonded to the adduct through a linker, wherein the linker is selected from the group consisting of a thiol linker and an amino acid linker.

21. The method of claim 6, wherein the therapeutically active compound in the conjugate is covalently bonded to the adduct through a linker, wherein the linker is selected from the group consisting of a thiol linker and an amino acid linker.

22. The composition of claim 20, wherein the thiol linker is a dithiol.

23. The composition of claim 22, wherein the dithiol is β-mercaptoethylether.

24. The composition of claim 20, wherein the amino acid linker is glycine.

25. The method of claim 21, wherein the thiol linker is a dithiol.

26. The method of claim 25, wherein the dithiol is β-mercaptoethylether.

27. The method of claim 21, wherein the amino acid linker is glycine.

* * * * *

UNITED STATES PATENT AND TRADEMARK OFFICE
CERTIFICATE OF CORRECTION

PATENT NO. : 8,071,535 B2
APPLICATION NO. : 10/571510
DATED : December 6, 2011
INVENTOR(S) : Yitzhak Tor It is certified that error appears in the above-identified patent and that said Letters Patent is hereby corrected as shown below:

Title Page, Column 2, Line 10, please delete "Critiical" and insert -- Critical --, therefor;

Title Page, Column 2, Line 19, please delete ""Nucelosides" and insert -- "Nucleosides --, therefor;

Title Page, Column 2, Lines 35-36, before "amino-substituted" please delete "and".

Column 60, Line 15 (Claim 17), before "dideoxycytidine" please insert -- 2',3'- --.

Column 60, Line 16 (Claim 18), please delete "claim 16," and insert -- claim 6, --, therefor.

Signed and Sealed this
Twenty-eighth Day of February, 2012

David J. Kappos
*Director of the United States Patent and Trademark Office*